(12) United States Patent
Kennedy et al.

(10) Patent No.: US 10,175,170 B2
(45) Date of Patent: *Jan. 8, 2019

(54) METAL COATING OF RARE EARTH NANO-PHOSPHORS AND USES THEREOF

(75) Inventors: Ian M. Kennedy, Davis, CA (US); Sudheendra Lakshmana, Davis, CA (US)

(73) Assignee: The Regents of the University of California, Oakland, CA (US)

(*) Notice: Subject to any disclaimer, the term of this patent is extended or adjusted under 35 U.S.C. 154(b) by 1144 days.

This patent is subject to a terminal disclaimer.

(21) Appl. No.: 13/993,658

(22) PCT Filed: Dec. 16, 2011

(86) PCT No.: PCT/US2011/065411
§ 371 (c)(1),
(2), (4) Date: Sep. 16, 2013

(87) PCT Pub. No.: WO2012/083133
PCT Pub. Date: Jun. 21, 2012

(65) Prior Publication Data
US 2013/0343997 A1    Dec. 26, 2013

Related U.S. Application Data

(60) Provisional application No. 61/423,996, filed on Dec. 16, 2010.

(51) Int. Cl.
| | | |
|---|---|---|
| A61K 33/16 | (2006.01) | |
| G01N 21/64 | (2006.01) | |
| B42D 25/20 | (2014.01) | |
| C09K 11/77 | (2006.01) | |
| D21H 15/02 | (2006.01) | |
| D21H 17/63 | (2006.01) | |
| D21H 19/02 | (2006.01) | |
| D21H 19/06 | (2006.01) | |
| D21H 21/48 | (2006.01) | |
| D21H 21/52 | (2006.01) | |
| A61K 9/14 | (2006.01) | |
| A61K 33/38 | (2006.01) | |
| A61K 49/00 | (2006.01) | |
| C09K 11/02 | (2006.01) | |
| H01F 1/01 | (2006.01) | |

(52) U.S. Cl.
CPC .......... *G01N 21/64* (2013.01); *A61K 9/14* (2013.01); *A61K 33/38* (2013.01); *A61K 49/0015* (2013.01); *A61K 49/0065* (2013.01); *B42D 25/20* (2014.10); *C09K 11/025* (2013.01); *C09K 11/77* (2013.01); *C09K 11/7766* (2013.01); *D21H 15/02* (2013.01); *D21H 17/63* (2013.01); *D21H 19/02* (2013.01); *D21H 19/06* (2013.01); *D21H 21/48* (2013.01); *D21H 21/52* (2013.01); *H01F 1/01* (2013.01); *B42D 2035/24* (2013.01)

(58) Field of Classification Search
CPC ........ A61K 9/51; A61K 49/00; A61K 49/001; A61K 49/0013; A61K 49/0015; A61K 49/0065; A61K 49/0093; A61K 33/16
See application file for complete search history.

(56) References Cited

U.S. PATENT DOCUMENTS

| | | |
|---|---|---|
| 5,154,852 A | 10/1992 | Chau |
| 5,156,764 A | 10/1992 | Kaneda et al. |
| 6,537,829 B1 | 3/2003 | Zarling et al. |
| 7,394,091 B2 | 7/2008 | Isobe et al. |
| 8,389,958 B2 | 3/2013 | Vo-Dinh et al. |
| 9,034,204 B2 | 5/2015 | Kennedy et al. |
| 2002/0119485 A1 | 8/2002 | Morgan |
| 2004/0014060 A1 | 1/2004 | Hoheisel et al. |
| 2005/0025969 A1 | 2/2005 | Berning et al. |
| 2006/0105170 A1* | 5/2006 | Dobson ............... B82Y 25/00 428/403 |
| 2007/0054120 A1 | 3/2007 | Meyer et al. |
| 2007/0212541 A1 | 9/2007 | Tsukada et al. |
| 2007/0212542 A1 | 9/2007 | Guo et al. |
| 2008/0011956 A1 | 1/2008 | Burrell et al. |
| 2008/0299667 A1 | 12/2008 | Kwok et al. |
| 2009/0007815 A1 | 1/2009 | Hampden-Smith et al. |
| 2009/0022766 A1 | 1/2009 | Geddes |
| 2009/0191128 A1 | 7/2009 | Ronda et al. |
| 2009/0227044 A1 | 9/2009 | Dosev et al. |

(Continued)

FOREIGN PATENT DOCUMENTS

| | | | |
|---|---|---|---|
| WO | WO 2006/064451 A2 | 6/2006 | |
| WO | WO 2011/084641 A2 | 7/2011 | |
| WO | WO-2011084641 A2 * | 7/2011 | ............. B82Y 30/00 |

OTHER PUBLICATIONS

Aslan, K., et al., "Metal-enhanced fluorescence using anisotropic silver nanostructures: critical progress to date," Anal Bioanal Chem, vol. 382, pp. 926-933, 2005.
Boyer, J.C., et al., "Synthesis of Colloidal Upconverting NaYF$_4$: Er$^{3+}$/Yb$^3$ and Tm$^{3+}$/Yb$^{3+}$ Monodisperse Nanocrystals," Nano Letters, vol. 7, No. 3, pp. 847-852, 2007.
Brown, K.R., et al., "Seeding of Colloidal Au Nanoparticle Solutions. 2. Improved Control of Particle Size and Shape," Chem. Mater., vol. 12, pp. 306-313, 2000.
Fu, Y., et al., "Plasmonic Enhancement of Single-Molecule Fluorescence Near a Silver Nanoparticle," J Fluoresc, vol. 17, pp. 811-816, 2007.
Graham-Rowe, D., "Nanoscale Inkjet Printing," Technology Review, MIT, Sep. 13, 2007, 3 Pages, [online] [retrieved on Jan. 23, 2010] Retrieved from the internet <http://www.technologyreview.com/news/408664/nanoscale-inkjet-printing/>.

(Continued)

*Primary Examiner* — Micah Paul Young
(74) *Attorney, Agent, or Firm* — Fenwick & West LLP

(57) ABSTRACT

Core-shell nanoparticles comprises a phosphorescent core and metal shell comprising at least two metals The phosphorescent core may comprise an up converting phosphor. The phosphorescent core may comprise a trivalent rare earth cation. The phosphorescent core further may comprise a monovalent alkali metal. The phosphorescent core may optionally comprises a second and also optionally a third trivalent rare earth cation.

12 Claims, 22 Drawing Sheets

(56) References Cited

U.S. PATENT DOCUMENTS

| | | | |
|---|---|---|---|
| 2010/0261263 A1* | 10/2010 | Vo-Dinh | A61L 2/08 |
| | | | 435/287.1 |
| 2011/0021970 A1 | 1/2011 | Vo-Dinh et al. | |
| 2011/0126889 A1 | 6/2011 | Bourke, Jr. et al. | |
| 2012/0286203 A1 | 11/2012 | Kennedy et al. | |

OTHER PUBLICATIONS

Hughey, J., "New Techniques for Generating Core-Shell Nanoparticles," NNIN REU Research Accomplishments, pp. 56-57, 2005.

Kuningas, K., et al., "Homogeneous Assay Technology Based on Upconverting Phosphors," Anal. Chem., vol. 77, pp. 7348-7355, 2005.

Lessard-Viger, M., et al., "FRET Enhancement in Multilayer Core-Shell Nanoparticles," Nano Letters, vol. 9, No. 8, pp. 3066-3071, 2009.

Ma, Z.Y., et al., "A microemulsion preparation of nanoparticles of europium in silica with luminescence enhancement using silver," Nanotechnology, vol. 20, No. 8, pp. 1-20, 2009.

Mai, H.X., et al., "High-Quality Sodium Rare-Earth Fluoride Nanocrystals: Controlled Synthesis and Optical Properties," Journal of the American Chemical Society, vol. 128, No. 19, pp. 6426-6436, 2006.

Morgan, C.G., et al., "Prospects for applications of lanthanide-based upconverting surfaces to bioassay and detection," Biosensors and Bioelectronics, vol. 22, pp. 1769-1775, 2007.

Patent Cooperation Treaty, International Search Report and Written Opinion, International Patent Application No. PCT/US2010/060856, dated Aug. 22, 2011, 13 Pages.

Patent Cooperation Treaty, International Search Report and Written Opinion, International Patent Application No. PCT/US2011/065411, dated Jun. 4, 2012, 10 Pages.

Schneider, G., et al., "Distance-Dependent Fluorescence Quenching on Gold Nanoparticles Ensheathed with Layer-by-Layer Assembled Polyelectrolytes," Nano Letters, vol. 6, No. 3, pp. 530-536, 2006.

Sudarsan, V., et al., "General and Convenient Method for Making Highly Luminescent Sol-Gel Derived Silica and Alumina Films by Using $LaF_3$ Nanoparticles Doped with Lanthanide Ions ($Er^{3+}$, $Nd^{3+}$, and $Ho^{3+}$)," Chem. Mater., vol. 17, pp. 4736-4742, 2005.

Turkevich, J., et al., "A Study of the Nucleation and Growth Processes in the Synthesis of Colloidal Gold," Discussions of the Faraday Society, No. 11, pp. 55-75, 1951.

Vetrone, F., et al., "Lanthanide-doped fluoride nanoparticles: luminescence, Upconversion, and biological applications," Int. J. Nanotechnol., vol. 5, Nos. 9/10/11/12, pp. 1306-1339, 2008.

Wang, K., et al., "Biomedical Applications Based on Core-Shell Nanoparticles," Proceedings of the IEEE $27^{th}$ Annual International Conference of the Engineering in Medicine and Biology, Shanghai, China, Sep. 1-4, 2005, pp. 717-719.

Wang, L., et al., "Fluorescence Resonant Energy Transfer Biosensor Based on Upconversion-Luminescent Nanoparticles," Angew. Chem. Int. Ed., vol. 44, pp. 6054-6057, 2005.

Yi, G., et al., "Synthesis, Characterization, and Biological Application of Size-Controlled Nanocrystalline $NaYF_4$:Yb, Er Infrared-to-Visible Up-Conversion Phosphors," Nano Letters, vol. 4, No. 11, pp. 2191-2196, 2004.

Zeng, H., et al., "Tailoring magnetic properties of core-shell nanoparticles," Applied Physics Letters, vol. 85, No. 5, pp. 792-794, 2004.

Zhang, J., et al., "Fluorescence Quenching of CdTeNanocrystals by Bound Gold Nanoparticles in Aqueous Solution," Plasmonics, vol. 3, pp. 3-11, 2008.

Deng, W. et al., "Upconversion in NaYF(4):Yb, Er Nanoparticles Amplified by Metal Nanostructures," Nanotechnology, Aug. 12, 2011, pp. 325604-, vol. 22, No. 32, May be retrieved at<URL:https://www.ncbi.nlm.nih.gov/pubmed/21772069>.

* cited by examiner

METAL COATING OF RARE EARTH NANO-PHOSPHORS AND USES THEREOF

This application is the 35 USC § 371 national stage entry of PCT/US2011/065411 and claims priority to and the benefit of the earlier filing date of U.S. Provisional Application 61/423,996 filed on Dec. 16, 2010, which is hereby incorporated by reference in its entirety for all purposes.

STATEMENT REGARDING FEDERALLY SPONSORED RESEARCH OR DEVELOPMENT

This invention was made with Government support under Grant No. 2009-35603-05070, awarded by the United States Department of Agriculture. The Government has certain rights in this invention.

SUMMARY OF THE INVENTION

A nanoparticle comprising a phosphorescent core and a metal shell comprising at least two metals is provided. In one embodiment, the phosphorescent core comprises an upconverting phosphor. In another embodiment, the phosphorescent core comprises a trivalent rare earth cation. In one embodiment, the phosphorescent core further comprises a monovalent alkali metal. The phosphorescent core optionally comprises a second and also optionally a third trivalent rare earth cation.

In one embodiment, the rare earth cation is $Tm^{3+}$, $Er^{3+}$, $Y^{3+}$, or $Yb^{3+}$.

In another embodiment, the phosphorescent core further comprises a Group 15, 16 or 17 anion. The Group 17 anion is $F^-$ in some embodiments.

In one embodiment the monovalent alkali metal is $Na^+$.

In one embodiment the at least two metals are transition metals. In another embodiment, the at least two metals are selected from the group consisting of Au, Ag, Pt, Pd, Rh and Re.

In one embodiment, nanoparticle further comprises a fluorescent tag.

In one embodiment, the nanoparticle further comprises a magnetic component.

In one embodiment the phosphorescent core comprises the magnetic component.

In one embodiment the magnetic component is magnetite ($Fe_3O_4$).

Also provided are methods of incorporating the nanoparticles into security paper.

Also provided is a security paper comprising a plurality of nanoparticles wherein said nanoparticles are visible and of a first color and upon excitation with a low-powered laser, said nanoparticles emit a second color.

In one embodiment, the second color emitted upon excitation is red, blue or green, or a combination thereof.

DETAILED DESCRIPTION

Figure 1:
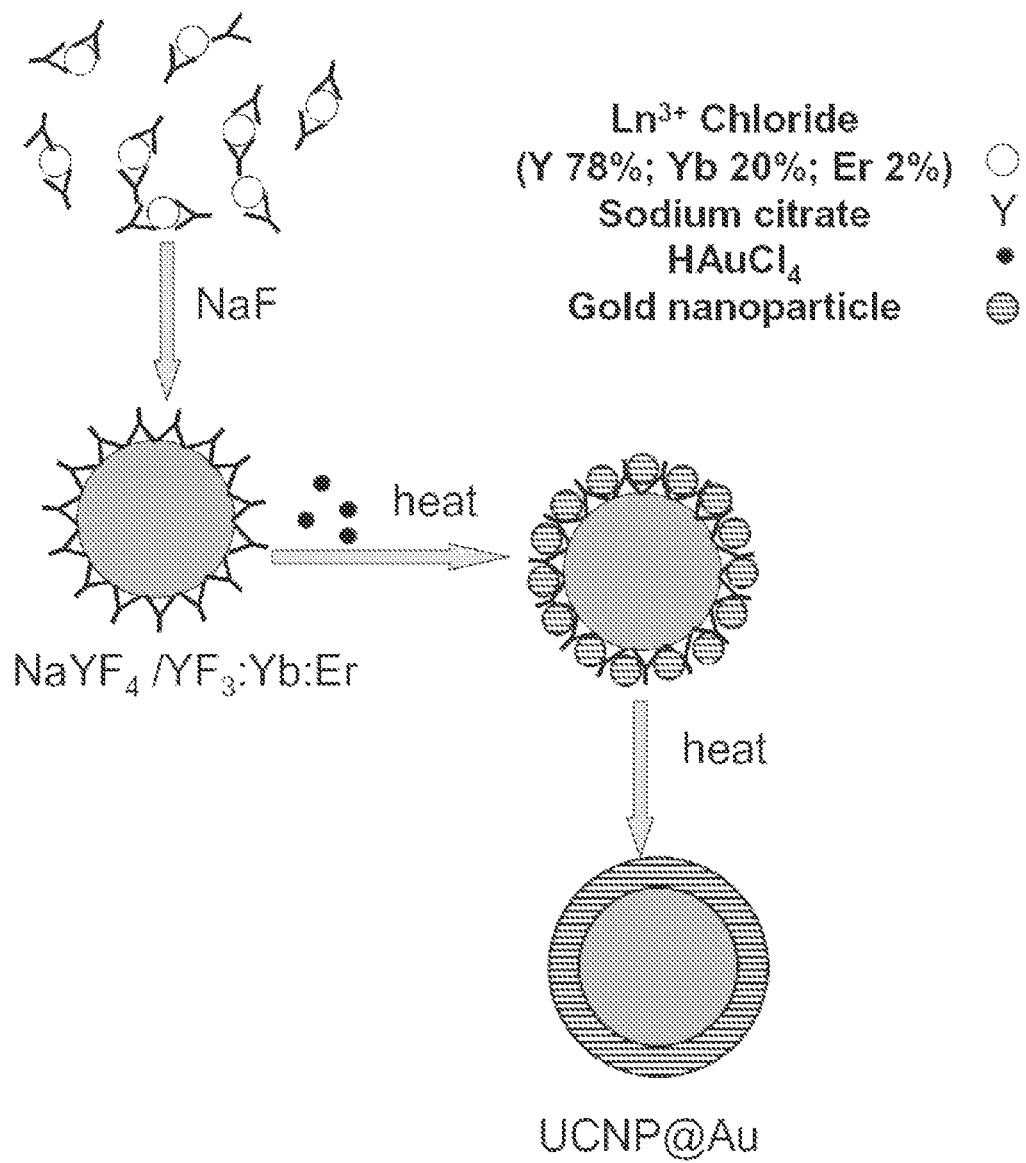
FIG. 1 is an illustration of the synthesis of gold-coated phosphor CSNP.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. The practice of the present invention will employ, unless otherwise indicated, conventional methods of chemistry and spectroscopy.

The rare earth elements are the lanthanide series, scandium (Sc) or yttrium (Y). The lanthanide elements are lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu).

A rare earth cation is the positive ion of one of the rare earth elements.

A transition metal is any element which has an incomplete d sub-shell or can give rise to cations with an incomplete d sub-shell.

A metal precursor is a compound that leads to the elemental metal in one or more reactions.

Numbering of the groups of the periodic table is according to the IUPAC recommendation of numbering groups of the periodic table with numbers 1-18.

An upconverting phosphor is a phosphor which emits radiation at a wavelength that is shorter than the excitation wavelength.

Förster Resonance Energy Transfer (FRET)

One of the most common optical detection techniques used for bioassays is fluorescence detection. Some of these techniques use an affinity based energy transfer phenomenon called Förster Resonance Energy Transfer (FRET) (sometimes referred to as Fluorescence Resonance Energy Transfer). A non-radiative energy transfer occurs between a donor and an acceptor depending on the distance between them and the overlap of the emission spectrum of the donor and the excitation spectrum of the acceptor. The transfer efficiency depends inversely on the sixth power of the distance between the donor and the acceptor molecule leading to a powerful nanoscale (2-10 nm) measurement technique. The transfer efficiencies for a wide variety of fluorescent dyes have been studied. Non-fluorescent quenchers such as QSY can also be used as efficient acceptors (donors) because of their availability in a wide spectrum range and the absence of any intrinsic fluorescence emission. FRET can be used as an efficient detection tool for fluoroimmunoassay applications. Antibody and antigen pairs can be tagged with FRET pairs, e.g., antibody with a fluorescent dye and antigen with its FRET pair; and used in different immunoassay formats including competitive assays. The binding reaction can be observed as a simultaneous decrease in the donor signal and an increase in the acceptor signal due to the energy transfer between the fluorescent dyes when they are in close proximity. If a non-fluorescent dye (quencher) is used as an acceptor, then only the decrease in the donor signal is observed relative to the reaction between the antibody-antigen.

A CSNP is one example of a biomarker that can be utilized with FRET. The core of the CSNP is a phosphor particle and the shell coating the core is metal. Rare earth, or lanthanide, cations are one example of a phosphor particle core that can be used with the teachings described herein. Rare earth ion phosphors are readily synthesized in different sizes, shapes and colors. Rare earth ions have an advantage over quantum dots as biomarkers, since some of the ions emit in the visible region (blue from Thulium, $Tm^{3+}$; green and red from Erbium, $Er^{3+}$) when excited by a near infrared light[1-3]. This phenomenon known as upconversion is not only inexpensive, but well-suited for labeling applications. Lower excitation energy of the phosphor eliminates auto fluorescence from most proteins, thereby eliminating unwarranted interference in quantification of interaction when the CSNP is used in bioassays. Förster resonance energy transfer (FRET) is a simple technique to detect interaction between biomolecules over a short range through the non-radiative transfer of energy from a donor to an acceptor molecule. Rare earth phosphor nanoparticles and organic fluorescent tags attached to DNA or protein may be an attractive system for FRET since a wide variety of nanoparticles is easily synthesized [4-6].

Metal nanoparticles are used in FRET based assays as promoters of resonance energy transfer between fluorophores [7]. The enhancement or suppression of fluorescence by the metal is dependent on the shape, size, distance and orientation of the nanoparticle [7-11]. Plasmonic and dielectric materials in a core-shell architecture can be employed to utilize the plasmonic enhancement of the fluorescence emission in a FRET configuration [9, 12].

Using two metals in the shell provides the opportunity for tuning of properties of phosphor CSNPs for particular applications. Adding the second metal can cause the shift in the plasmon absorption peak. For example, nanoparticles of gold have plasmon absorption peaks that are predominantly observed at wavelengths ≥500 nm. Adding silver to gold changes the absorption peak to wavelengths ≤500 nm. The absorption peak shifts to higher wavelengths with increasing metal nanoparticle size or the core size on which they are coated. One can understand that using two metals, 1) the color of the phosphor CSNPs can be tuned from blue to NIR. 2) the color of the phosphor CSNPs can be made the same for different phosphor core sizes by a suitable choice of the two metals, their size and amounts. The changes in the composition of the metals influences the absorption and emission characteristics of the phosphor core. Apart from the plasmonic effects of the metal, the crystal fields around activators and emitters are influenced by phonons. The type of metal, their size and amount, in and around the phosphor selectively affects the different emissions from the phosphor to generate a specific color. Incorporation of silver as the second metal adds antifungal and antibacterial properties to the phosphor CSNPs. Since silver has a lower melting point, sintering of phosphor CSNPs can be achieved at lower temperatures. The sintered phosphor CSNPs will result in new ceramic (dielectric)-metal compositions (composites) with unique optical and conductive properties.

In one embodiment, the CSNPs include magnetic or super-paramagnetic particles. This component provides a handle to manipulate the particle and can also play a role as a functional adduct in providing a magnetic signal in immunoassays when used as sensors. Further, they allow manipulating and sorting particles or analytes in micro- or nanofluidic devices. In embodiments where the CSNP is used for magnetic hyperthermia therapy the magnetic component is useful in heat generation. Magnetic particles for use with the disclosed gold-coated phosphor CSNPs include magnetite (Fe3O4), rare earth elements including Nd, Sm and Gd and alloys including Fe, B or other non-lanthanide elements.

EXAMPLES

Example 1—Preparation and Characterization of Gold-Coated CSNPs

FIG. 1 illustrates the synthesis of the gold-coated phosphor CSNP. In FIG. 1, $Ln^{3+}$ is the representative rare earth trivalent cation. The CSNP is prepared by a solution based technique. A 0.2 M solution of $YCl_3$ (78% by molecular weight), $YbCl_3$ (20%) and $ErCl_3$ (2%) was mixed with 0.2 M sodium citrate in a 1:2 volume ratio and heated to 90° C. 1 M NaF was added at four times the volume of the solution forming a white colored solution. Then 380 nmoles of 0.1% $HAuCl_4$ were added and the heating was continued for two and half hours resulting in gold-coated $NaYF_4$ nanoparticles containing $Yb^{3+}$ and $Er^{3+}$ that were pink in color. The nanoparticles were centrifuged and dried at 80-100° C. resulting in a xerogel. The xerogel was crushed and heated to 450° C. for 12 hours under continuous nitrogen flow in a custom built tubular furnace.

Figure 2:
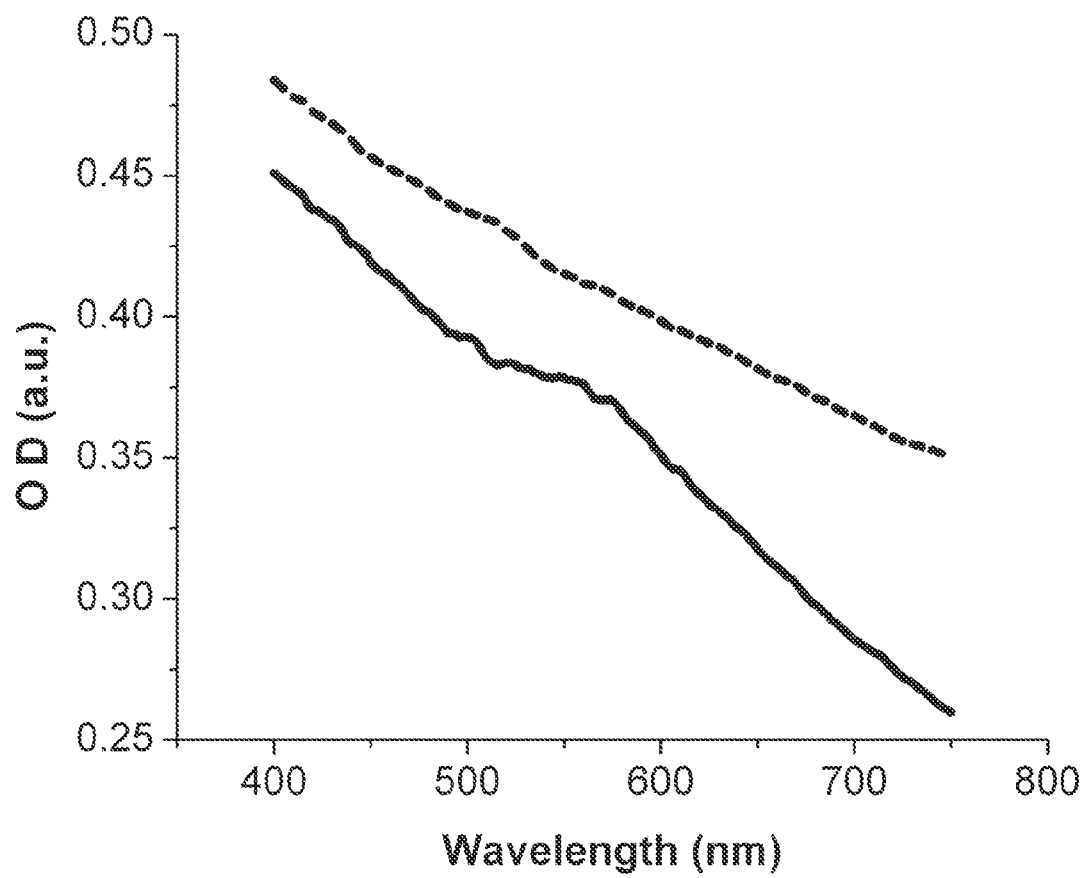
FIG. 2 is an absorbance spectrum of 0.1% solution of gold-coated phosphor CSNP.

The resulting gold-coated phosphor CSNPs were characterized by creating a 0.1% solution in water. The absorbance was measured by a SPECTRAMAX™ M2 from Molecular Devices in Sunnyvale, Calif. The results are shown in FIG. 2. The solid line represents absorbance of the gold coated CSNPs and the dashed line represents absorbance of the nanoparticle prior to the gold coating. The discontinuity in the absorbance of the gold coated CSNP between 500 and 600 nm arises from the gold surface plasmon resonance providing evidence that the gold shell has been deposited.

Figure 3:
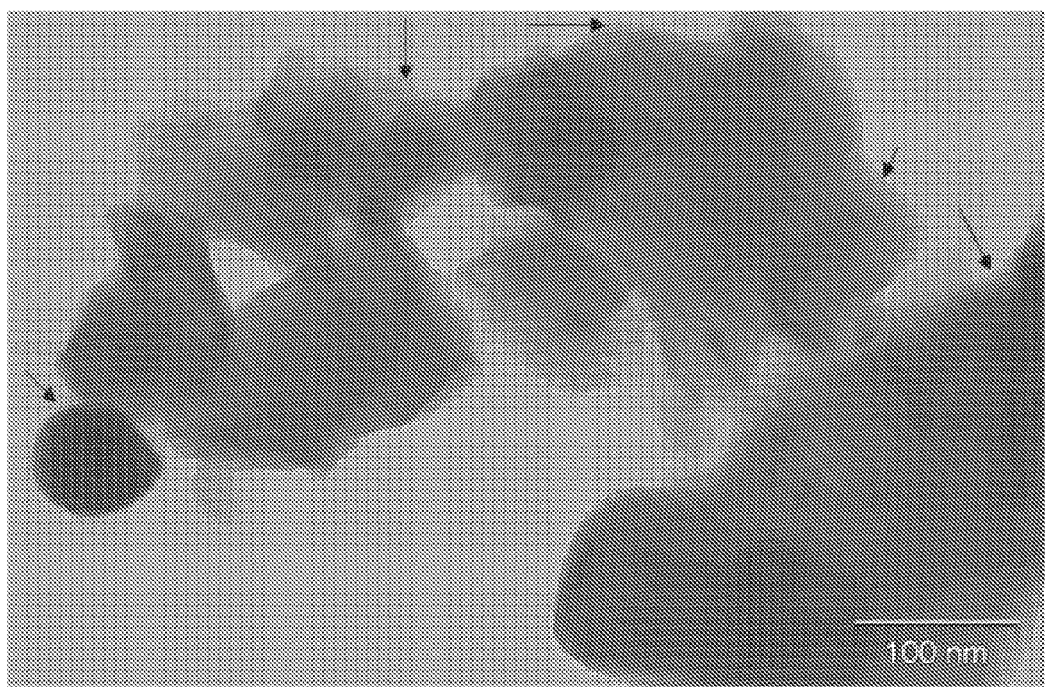
FIG. 3 is a transmission electron micrograph image of gold-coated phosphor CSNP heated to 450° C.

Additionally the CSNPs were heated to 450° C. and imaged by transmission electron microscopy (CM-12 scanning transmission electron microscope from Philips in Eindhoven, Netherlands). FIG. 3 is the transmission electron micrograph. The arrows point to the thin layer of gold of 4-8 nm surrounding the phosphor. These nanoparticles displayed green and red color emissions when excited by 975-980 nm operated at an average power of 22 mW (±0.5 mW).

Example 2—Additional Nanoparticles

A 0.2 M solution of $YCl_3$ (78% by molecular weight), $YbCl_3$ (20%) and $ErCl_3$ (2%) was mixed with 0.2 M sodium citrate and 1 M NaF (Sigma Aldrich) solution in a 1:2:4 volume ratio and heated to 90° C. Then 1.52 μmoles of 0.1% $HAuCl_4$ (Alfa Aesar) were added to the white colored solution, and the heating was continued for two and half hours. The synthesis of core nanophosphor (without gold coating) was done with the same above procedure without the addition of the $HAuCl_4$, resulting in white colored nanoparticles. Both sets of nanoparticles were centrifuged and dried at 80-100° C. The resulting xerogel was crushed and heated to 350° C. for 12 h in N2 flow furnace.

Figure 4:
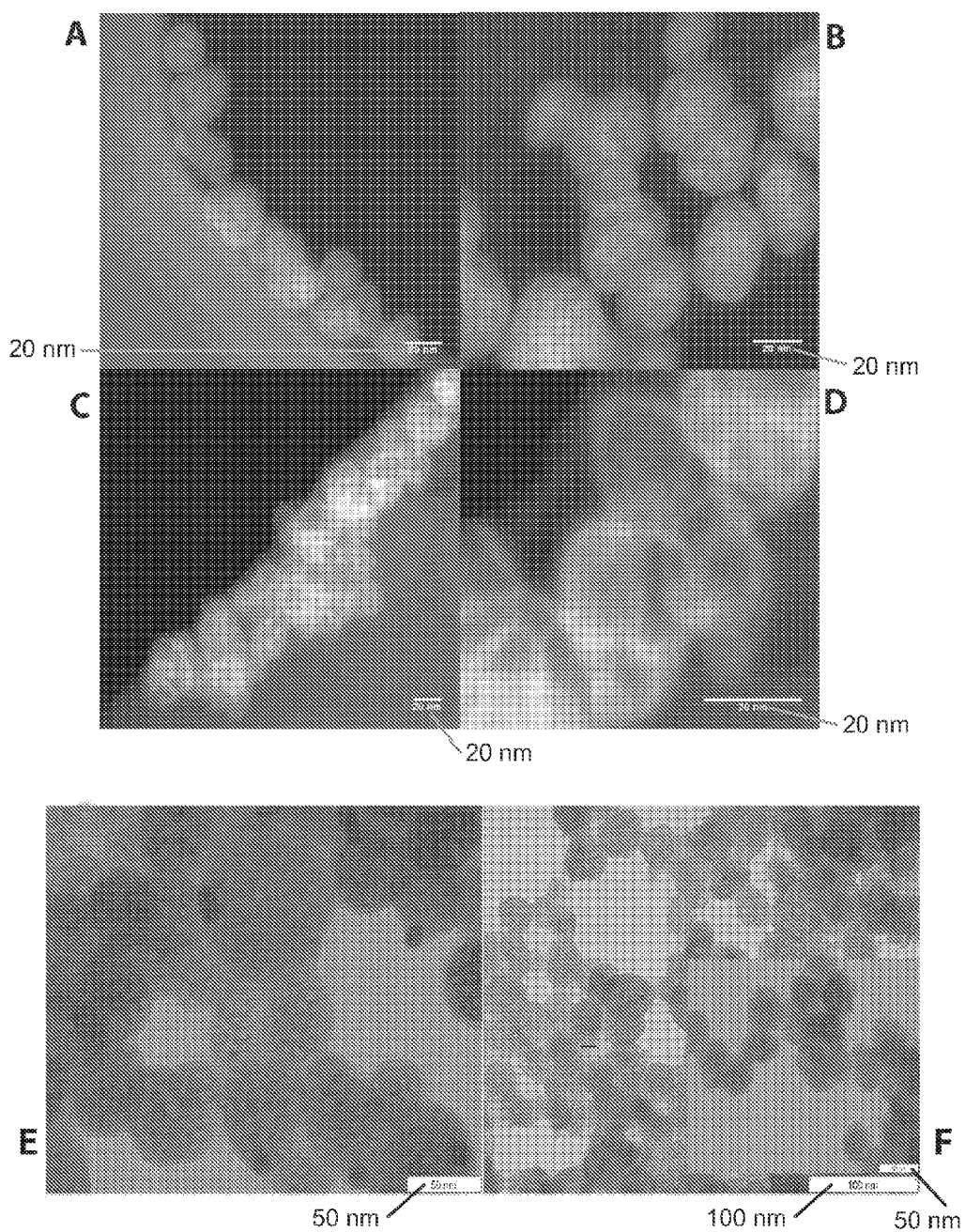
FIG. 4 are HAADF-STEM micrographs of gold-coated and uncoated phosphor CSNPs.

Transmission electron microscopy in which strong atomic-number (Z) contrast verifies the presence of gold was used to analyze the resulting nanoparticles. In Z-contrast imaging, the contrast in the image is dependent on the atomic number of the observed atom with intensities roughly proportional to Z2.[13] The powder samples were deposited on a formvar/carbon coated copper grids from a water solution, dried before taking the bright field transmission electron micrographs from Phillips CM-12 operating at 120 KeV and 15 mA. The HAADF-STEM images were taken using a field emission gun JEOL JEM 2500SE (S)TEM instrument operated at 200 kV with a 1 nm spot size and 800 mm camera length, corresponding to an inner and outer semi-collection angle of 35 and 90 mrad, respectively. FIG. 4 shows the Z-contrast images from scanning transmission electron microscopy (STEM). FIGS. 4a and 4b show the uncoated $NaYF_4$:20% Yb:2% Er nanophosphors. FIGS. 4c and 4d show the core-shell architecture of the gold-coated nanophosphors. In FIGS. 4c and 4d, the gold shell was visible on top of the NP core. Due to the atomic number difference between the yttrium (Z=39) core and the gold (Z=79), the gold shell appears as a 'bright ring' on top of the core. This was further verified by imaging the uncoated NP in the same mode (FIGS. 4a and 4b). Such bright features were absent—confirming the formation of gold coated NPs. The particle sizes of both coated and uncoated NPs were similar at about 20-50 nm; the particles appeared to be porous in nature. From the bright field TEM micrographs, no secondary nanoparticle phase that could be attributed to the gold nanoparticles is visible, even as the gold precursor was increased stepwise in the solution. This can be attributed to the fact that the reductant citrate ion is not present in the solution but is confined to the surface of the core NP—the nucleation rate in the solution is minimized, and is enhanced on the surface of the core.14 Optimization of the gold coating method to avoid nucleation of the gold nanoparticles was achieved by varying the concentration of the $HAuCl_4$ solution. A dilute solution of 0.1% eliminated the growth of Au nanoparticles (FIG. 4f) on the surface and enhanced the formation of the shell when compared to 1% solution (FIG. 4e).

Figure 5:
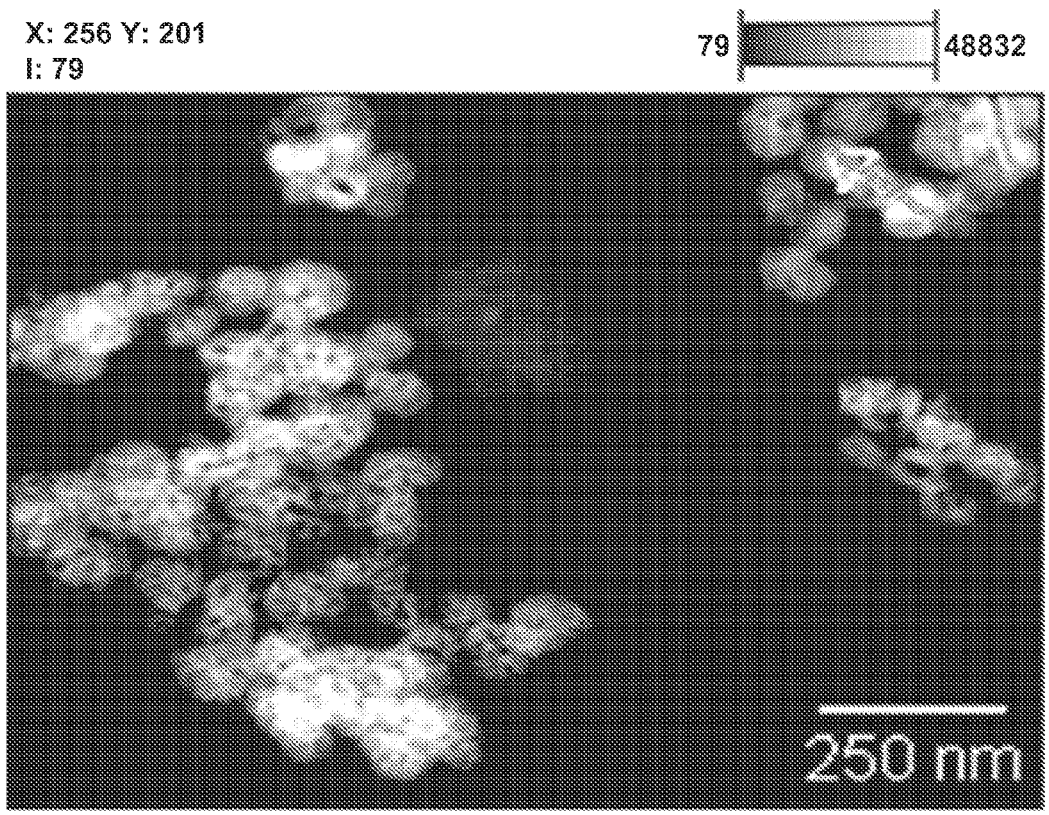
FIG. 5 is an additional HAADF-STEM image for gold-coated phosphor CSNPs with accompanying EDS line spectra.
Figure 5:
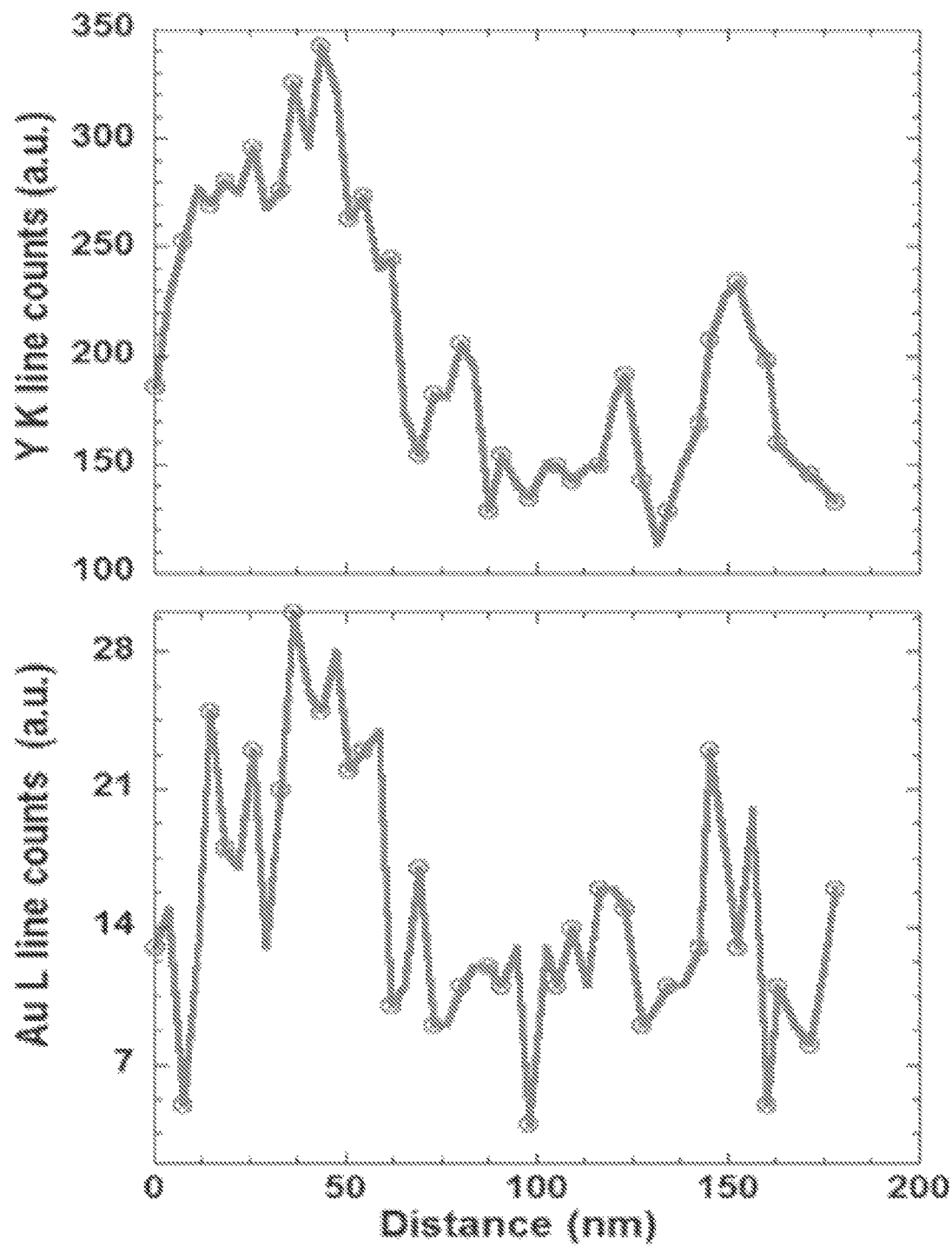
Figure 6:
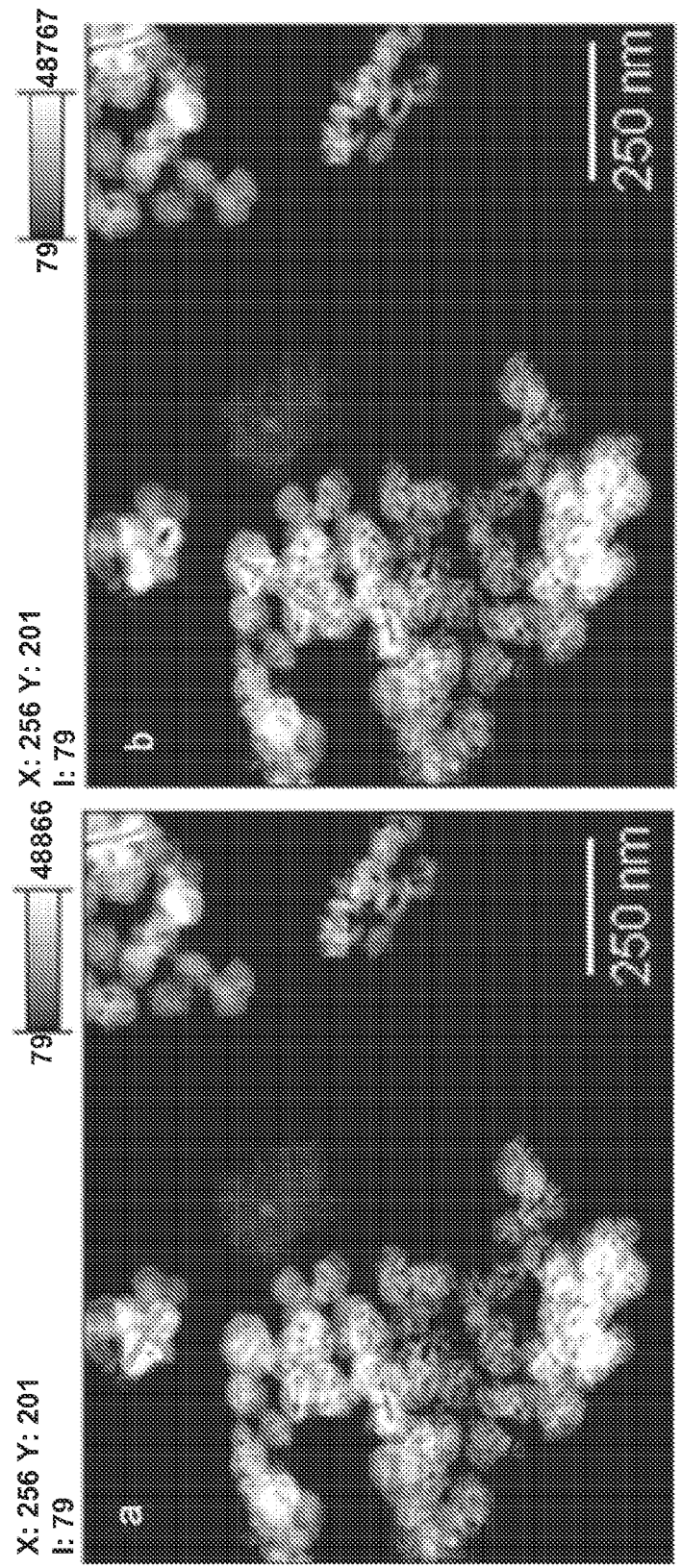
FIG. 6 are additional HAADF-STEM images for gold-coated phosphor CSNPs with accompanying EDS line spectra.
Figure 6:
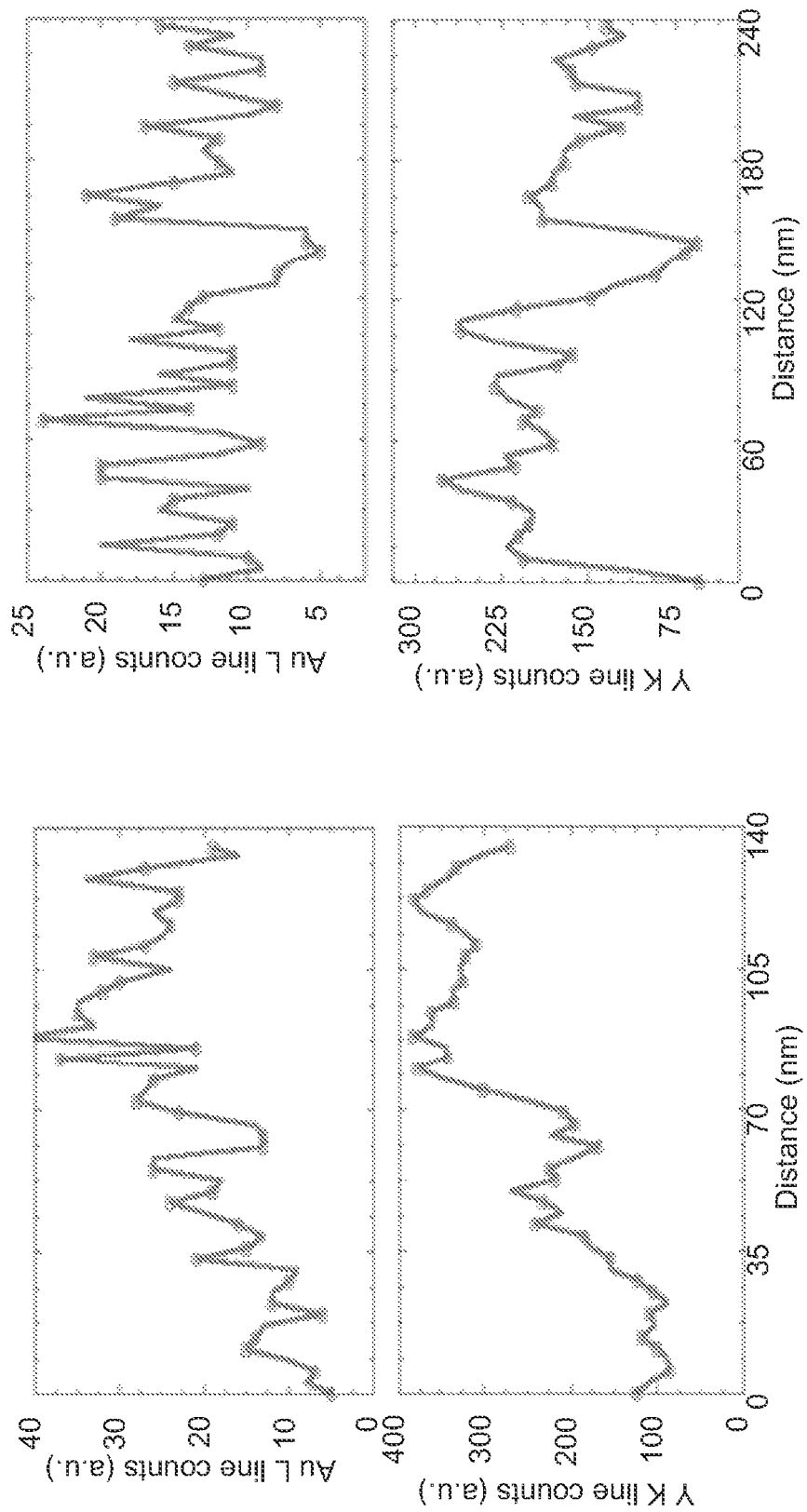

FIGS. 4c and 4d show continuous gold shells of 4-8 nm achieved using the highest concentration of 0.1% $HAuCl_4$ precursor in the solution, corresponding to Au/Tm and Au/Er of 0.19 and 0.095. There is minimal variation across various nanoparticles as demonstrated by the EDS spectra in FIG. 5. EDS spectra in FIG. 5 from different nanoparticles provide a semi-quantitative confirmation of the Au shell uniformity, where the ratio of Au to Y was ~0.07 when integrated area under the curves are considered (See also FIG. 6 of additional HAADF-STEM images and EDS spectra for gold-coated phosphor CSNPs).

Powder X-Ray Diffraction

Figure 7:
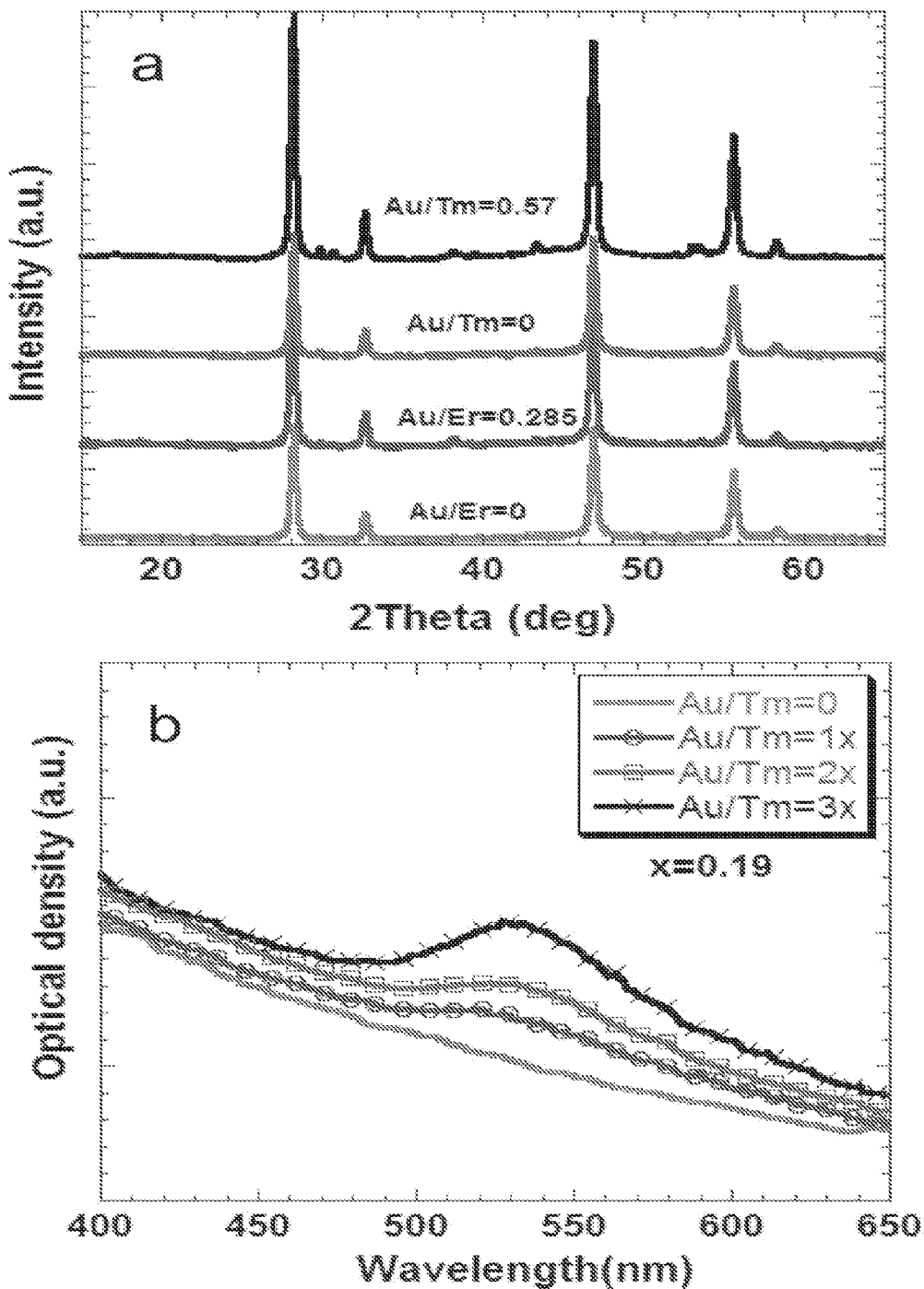
FIG. 7 are X-ray diffraction and optical absorbance measurements for gold-coated and uncoated phosphor CSNPs.
Figure 8:
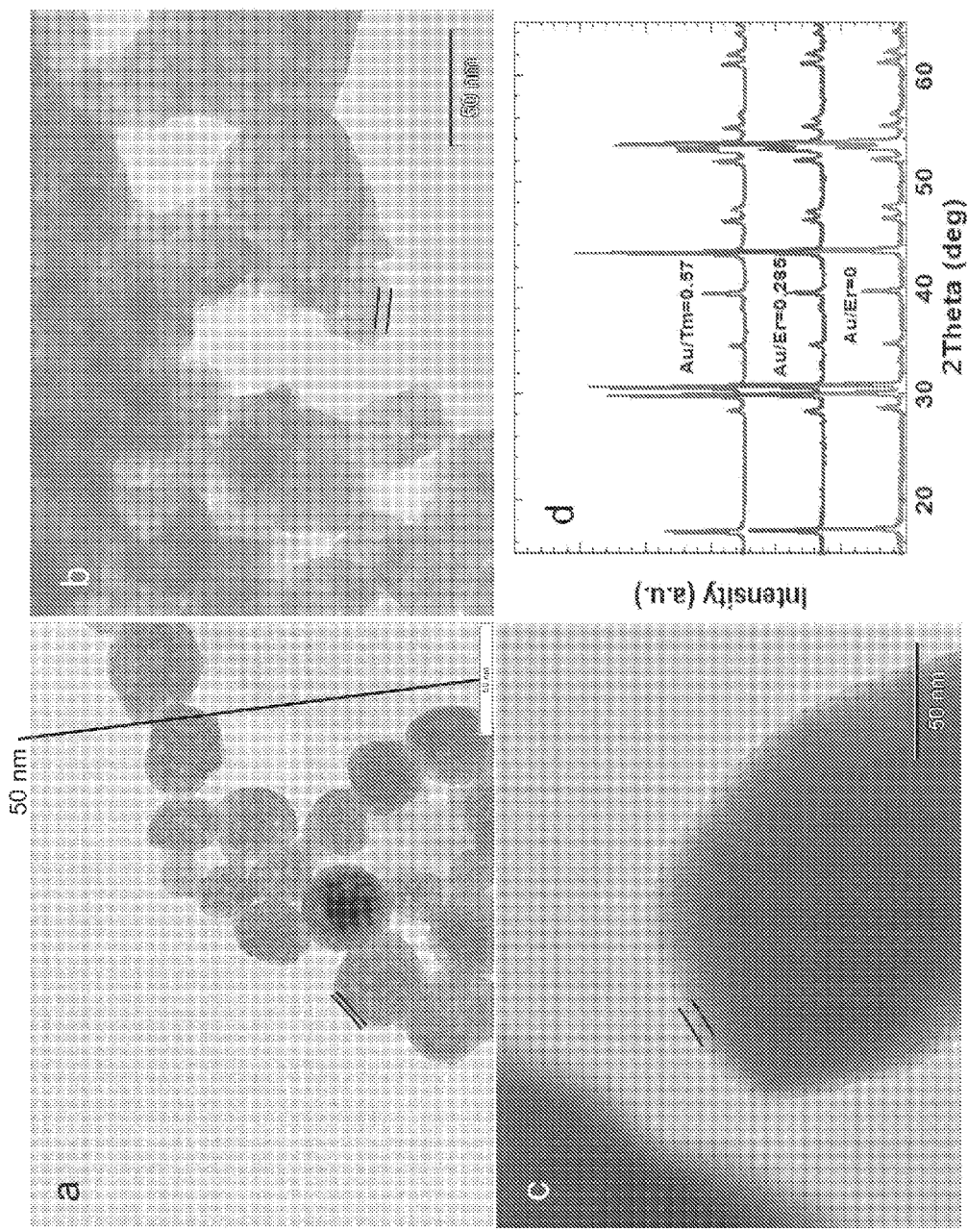
FIG. 8 are bright field TEM micrograph images for heated gold-coated phosphor CSNPs and X-ray diffraction data.

The phases of the calcined powders of gold-coated and uncoated phosphor CSNPs were characterized by Sintag XDS 2000 fitted with a copper Kα source, operating at −45 KV and 40 mA. Powdered samples were spread on a low background glass slide and scanned in a 2θ-2θ geometry from 10 to 60 degrees. FIG. 7a shows X-ray diffraction data for both gold-coated and uncoated cubic α-$NaYF_4$ (JCPDS-77-2042) nanophosphors containing $Er^{3+}$ and $Tm^{3+}$ heated to 90° C. for 12 h. The presence of the Au shell was not detected from X-ray diffraction and it appears that the Au shell is amorphous. Even the heating of the gold-coated phosphor CSNPs to 350° C. did not result in the crystallization of the Au shell (FIG. 8b). However, the $NaYF_4$:Yb:Er/Tm was cubic α phase when synthesized and dried at 90 C (FIG. 7a).

The gold-coated and the uncoated phosphor CSNPs ($NaYF_4$:20% Yb:2% Er and $NaYF_4$:20% Yb:1% Tm) were heated to 350° C. for four hours in a tubular furnace under a controlled nitrogen atmosphere. To maintain the same heat treatment all samples were heated in a batch, thus subjecting both to the same conditions. The X-ray diffraction (FIG. 8d) of the heated samples show that the phase of the nanoparticle is a mixture of α (JCPDS-77-2042) and β JCPDS-39-0724) $NaYF_4$ phases, with β $NaYF_4$ being the dominant phase. The effect of heat treatment can be quantified from the ratio of X-ray intensities arising from the (220) and (111) planes, corresponding to 100% intensities of α and β $NaYF_4$ phases, respectively. In the coated and uncoated cases, the ratio of intensity, I(220)α/I(111)β, was 3.5 and 3.2 respectively. Given the inhomogeneous distribution of the two phases in the sample, and the error in the amount of sample exposed to X-rays, the two phases in the coated and the uncoated can be considered to be effectively equal.

A distinct shell of 4-8 nm is visible in the bright field TEM micrograph of the calcined gold coated NP (FIG. 8a-c; FIGS. 8a and 8b are $NaYF_4$:20% Yb:2% Er with Au/Er ratio of 0.095 with 8a heated to 90° C. for 12 hours and 8b heated to 350° C. for four hours; FIG. 8c is $NaYF_4$:20% Yb:2% Er with Au/Er ration of 0.285 heated to 350° C. for 12 hours).

Absorbance and Emission Experiments

Figure 9:
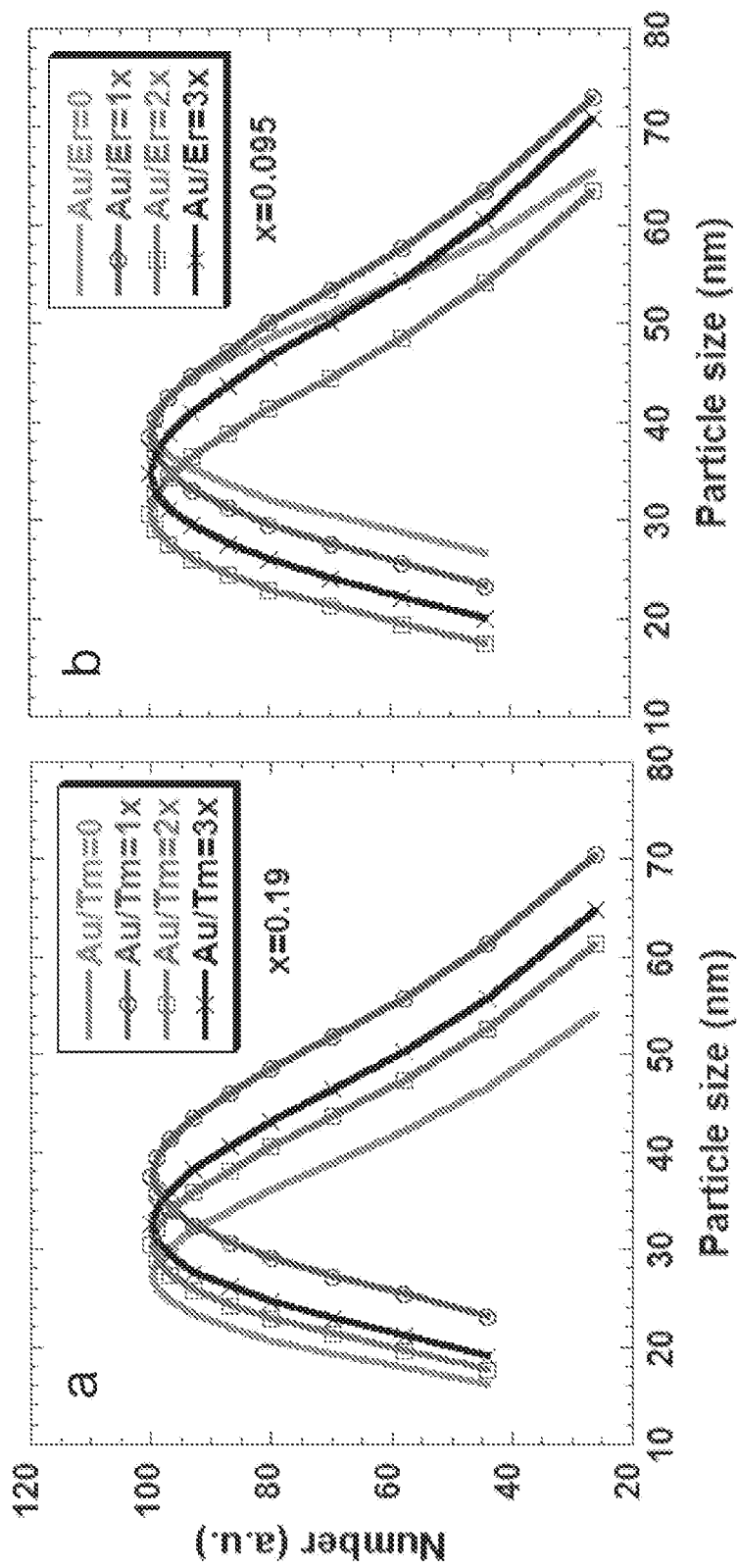
FIG. 9 are particle size distributions from dynamic light scattering experiments.

The absorbance and emission experiments were performed with 0.1% solution of the colloids prepared using cubic α-NaYF4:20% Yb:1% Tm and cubic α-NaYF4:20% Yb:2% Er nanophosphors dried at 90° C. for 12 h. The CSNPs had varying ratios of Au to Tm/Er as shown on the graphs of FIG. 9. The colloids were characterized by dynamic light scattering experiments (Brookhaven ZetaPlus) for aggregation. A single run was of two minutes duration and the data was averaged over five runs for each sample. The colloidal suspension has a particle size distribution corresponding to the primary particle size of the nanophosphors (FIG. 9).

Figure 10:
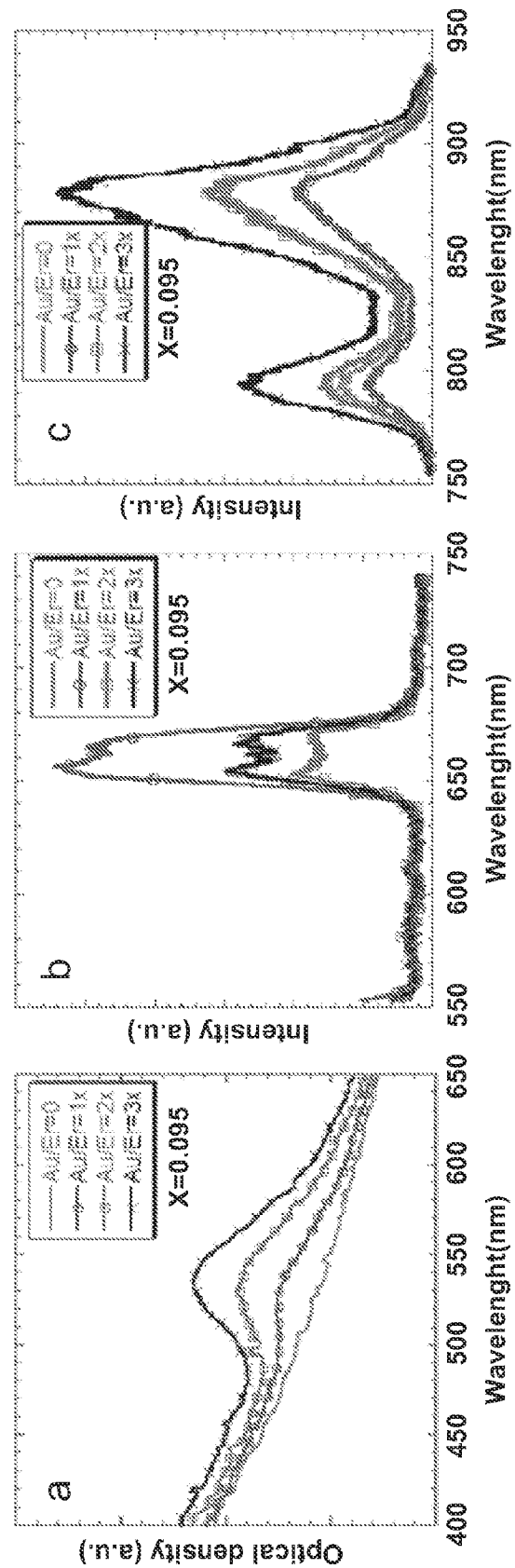
FIG. 10 shows absorbance and up-conversion emission spectra for gold-coated and uncoated phosphor CSNPs.

The absorbance of this solution was measured by spectramax M2 from Molecular Devices in a quartz cuvette. FIG. 7b shows the absorbance measured from the gold-coated and uncoated, Tm containing, α-NaYF$_4$ nanophosphors with a maximum at around 525 nm as well as the uncoated nanophosphors. The Au/Tm(Er) ratio is the molar ratio of Au$^{3+}$ and Tm$^{3+}$ (Er$^{3+}$) in the reaction mixture. The absorbance increases with the concentration of the 0.1% HAuCl$_4$ in the solution with Au/Tm ratio of 0.57 corresponding to easily decipherable shell thickness of 4-8 nm. While the uncoated nanophosphors did not show any maximum due to absorbance, a scattering indicated by exponential decay with increasing wavelength was observed. The observations were similar for Er containing nanophosphors. FIG. 10a shows optical absorbance of 0.1% solutions of cubic α-NaYF$_4$: 20% Yb:2% Er with different gold coatings. FIG. 10b shows up-conversion emission in the red when excited by 975 nm. FIG. 10c shows up-conversion emission in the near infrared also upon excitation with 975 nm.

Upconversion emission experiments were performed by a continuous wave laser (Lasermate) operating at 975 nm. The PTG (Princeton instruments controlled the shutter on the Princeton Instruments PI-MAX camera fitted with a charge-coupled device sensor. The photons emitted by the upconverting NP were focused on to Acton spectrapro 300i series spectrometer by objective and condensing lenses. The controller, the camera and the spectrometer were synchronized by Winview/32 software provided by Princeton Instruments. Quartz cuvette was used in all experiments and the laser with a power density of 67 W/cm-2 was focused on the quartz cuvette and the emission collected by a combination of condensing lens that focused the light on the slit of the spectrometer.

Figure 11:
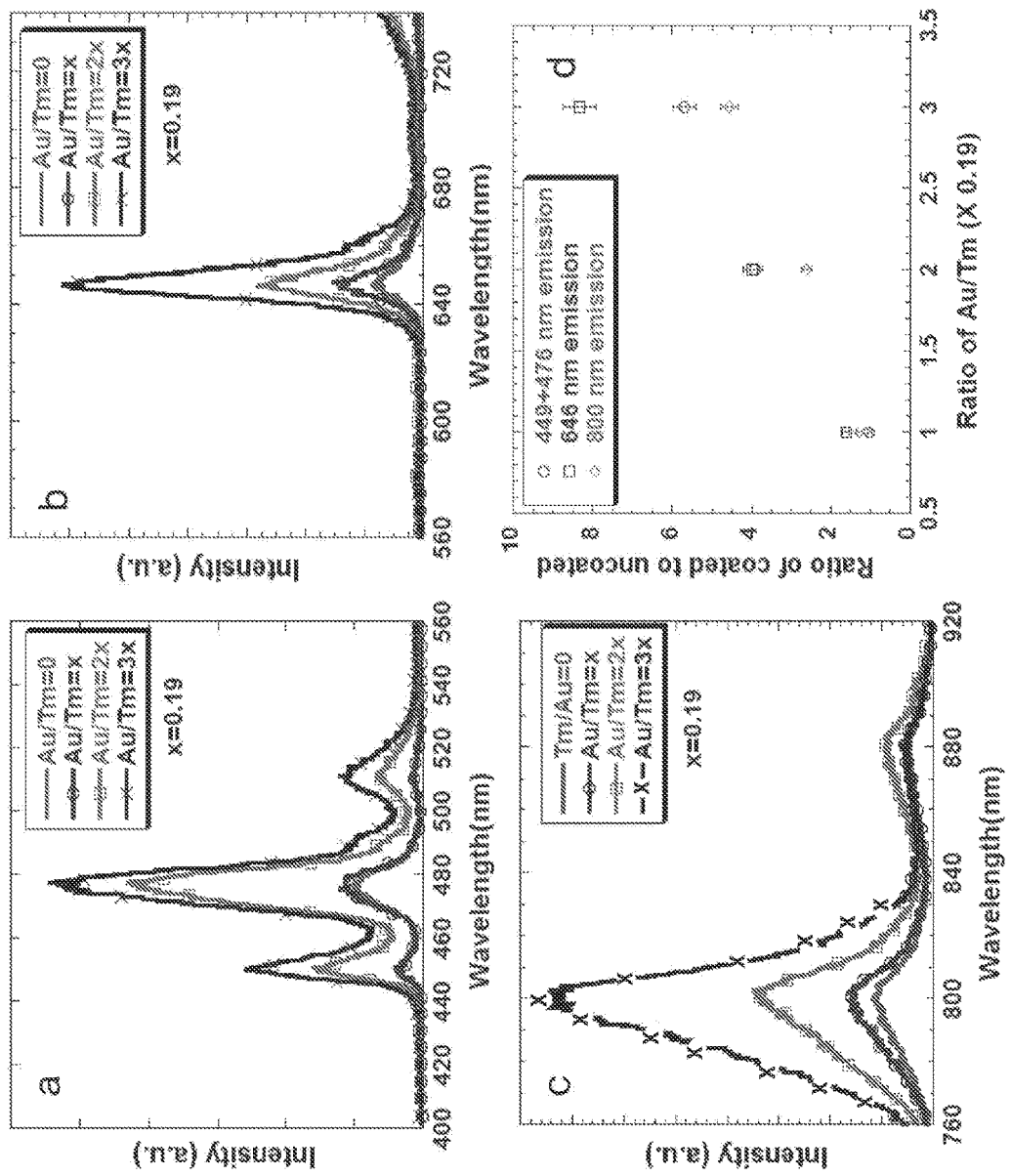
FIG. 11 shows absorbance and up-conversion emission spectra for gold-coated and uncoated phosphor CSNPs.
Figure 12:
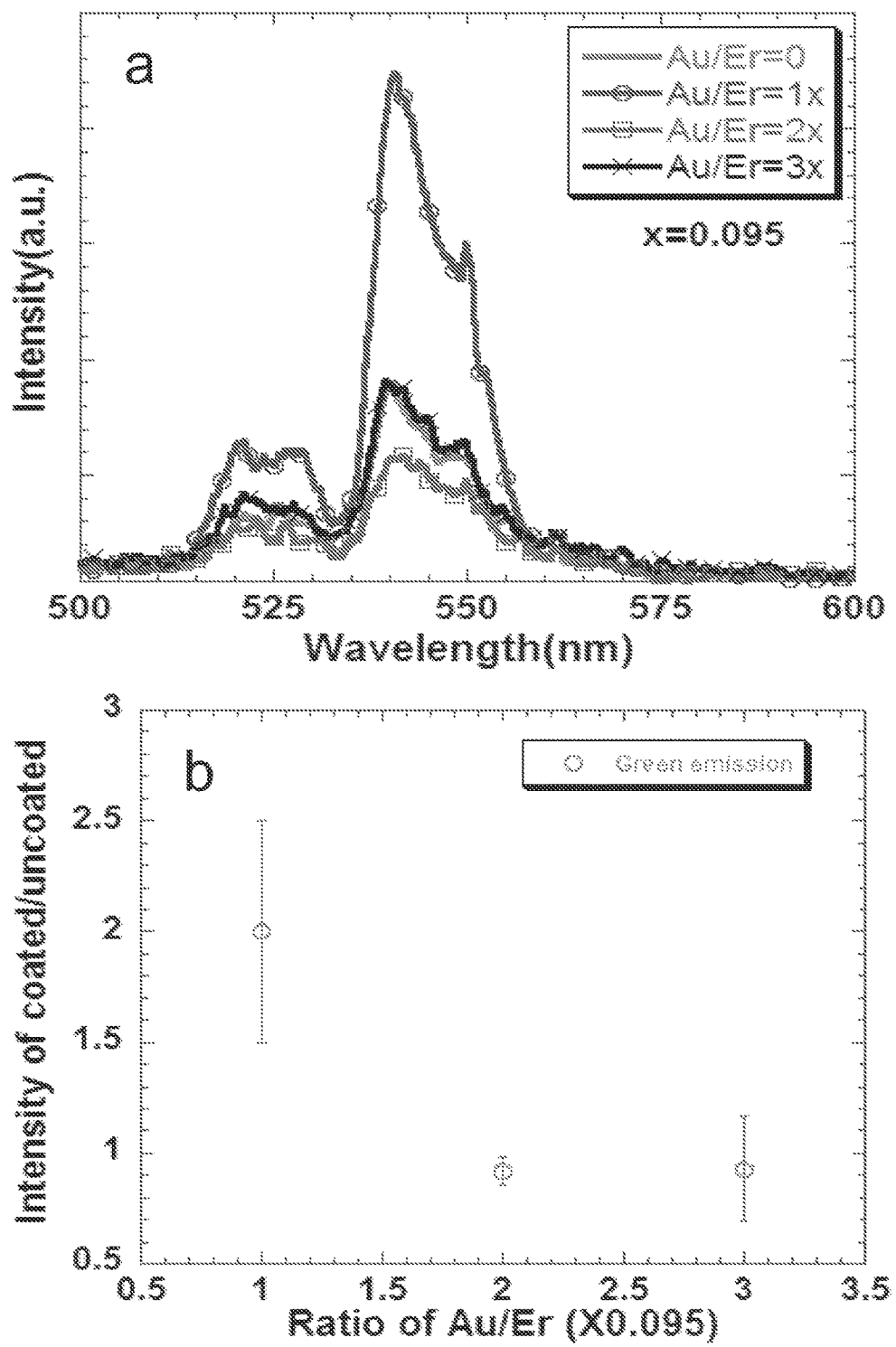
FIG. 12 shows up-conversion emission spectra for gold-coated and uncoated phosphor CSNPs.

FIG. 11a-c show the up-conversion emission characteristics of gold coated and uncoated 0.1% solution of cubic α-NaYF$_4$:20% Yb:1% Tm nanophosphors excited at 975 nm. FIG. 11d is an integrated area of the emission spectra from gold-coated phosphors normalized to the uncoated phosphor. With increasing concentration of 0.1% HAuCl$_4$ in the reaction mixture, the blue ($^1D_2 \rightarrow ^3F_4$ and $^1G_4 \rightarrow ^3H_6$), red ($^1G_4 \rightarrow ^3F_4$) and the near-infrared ($^3H_4 \rightarrow ^3H_6$) emission intensities shows a systematic increase with no quenching effect attributable to the presence of complete nanoshells of on top of the nanophosphors.15 The two different samples tested had an error less than 5%, which was the uncertainty in the power output of the laser. Hence the error is represented as the percentage of the value. However, with Er doped nanophosphors, it appears that the plasmonic enhancement is limited to low concentrations of HAuCl4 and hence lower concentration of Au on the surface of the nanophosphor. FIG. 12a shows up-conversion emission from 0.1% solutions with different gold coatings on cubic α-NaYF4:20% Yb:2% Er excited at 975 nm. FIG. 12b is an integrated area of the emission spectra from gold-coated phosphors normalized to the uncoated phosphor. In Er containing nanophosphors (FIG. 12), with Au/Er ratio of 0.095, there is a two-fold increase in the emission of green ($^2H_{11/2} \rightarrow ^4I_{15/2}$ and $^2S_{3/2} \rightarrow ^4I_{15/2}$) and red emission ($^4F_{9/2} \rightarrow ^4I_{15/2}$) and suppression of the near-infrared emission ($^2S_{3/2} \rightarrow 4I_{13/2}$) (FIG. 10), while for higher concentrations the of gold the intensities of emissions are comparable. The error bars in the plot correspond to the standard deviation from three different samples. This could be due to competing effect of the plasmonic fields and inner filter effect of the plasmonic shell that have absorbance around 530 nm. It should be noted that the plasmonic enhancement of up-conversion in an Er$^{3+}$ containing NaYF$_4$ has been achieved by carefully arranging NPs and plasmonic nanoparticles using atomic force microscopy.[16]

It should be noted that the two sets of emission $^1G_4 \rightarrow ^3H_6$, $^1G_4 \rightarrow ^3F_4$ and $^2S_{3/2} \rightarrow ^4I_{15/2}$, $^2S_{3/2} \rightarrow ^4I_{13/2}$ for Tm and Er, respectively have the same initial state in their respective ions, but the gold shell has quite different influence on the two emissions. In Tm containing nanophosphors, the plasmonic effect is positive with the enhancement of both the emissions, while for Er the higher energy transition, $^2S_{3/2} \rightarrow ^4I_{15/2}$, is enhanced and the $^2S_{3/2} \rightarrow 4I_{13/2}$ is suppressed, showcasing the subtleties of the plasmonic field effects on energies of emissions. This interplay between emission and plasmonic shell suggests the probable direct coupling of the Plasmon electric fields to the energy level of the emission electron.

Example 3—Preparation of Labeled Gold-Coated CSNPs

Figure 13:
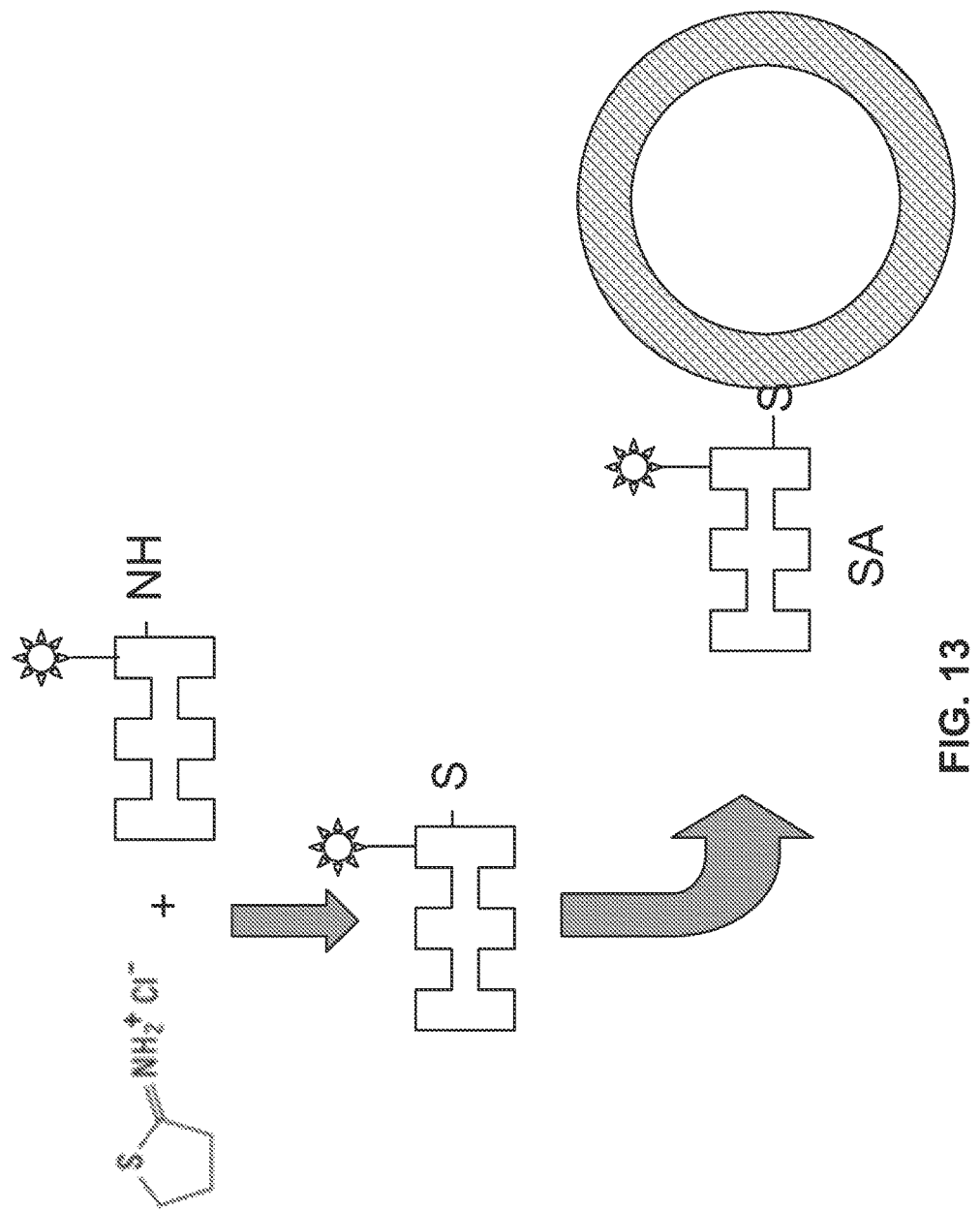
FIG. 13 illustrates the process of labelling gold-coated phosphor CSNP with streptavidin-tetramethylrhodamine (SA-TMR).

SA and SA-TMR conjugate (from Invitrogen in Carlsbad, Calif.) is adsorbed onto gold-coated phosphor CSNPs. FIG. 13 provides an illustration of the labeling process. Gold-coated phosphor CSNPs were prepared as described previously. 500 μl of 0.005% SA and SA-TMR in 10 mM phosphate buffered silane (PBS) was reacted with 50 μl of 50 mM 2-iminothiolane HCl (Traut's reagent). The reaction was facilitated by stirring and allowed to proceed under ambient conditions in a dark environment for two hours. Different volumes of 0.1% gold-coated phosphor CSNP were introduced and stirred continuously for 10-12 h.

The effectiveness of binding was established by comparing the control solution with the supernatant obtained after isolating the gold-coated phosphor CSNP from the reaction mixture in a FRET experiment. To this end, control solutions of 0.005% SA and SA-TMR containing Traut's reagent were suitably diluted by double distilled deionized water to match the different volumes of gold-coated phosphor CSNP solution. The absorbance was determined of the supernatant obtained after isolating the gold-coated phosphor CSNP conjugated with SA and SA-TMR by centrifugation at 3500 rpm for 6 min. 600 ml of the solutions (supernatant and control) were taken and diluted to 1 ml before taking the absorbance. For comparison, absorbance of the 0.1% gold-coated phosphor CSNP without conjugation with SA or SA-TMR was also measured. The absorbance spectra is shown in FIG. 14 wherein the open circles represent absorbance of the supernatant extracted after conjugation with gold-coated phosphor CSNP and the closed circles represent 0.003% SA-TMR conjugate in 6 mM PBS.

Figure 14:
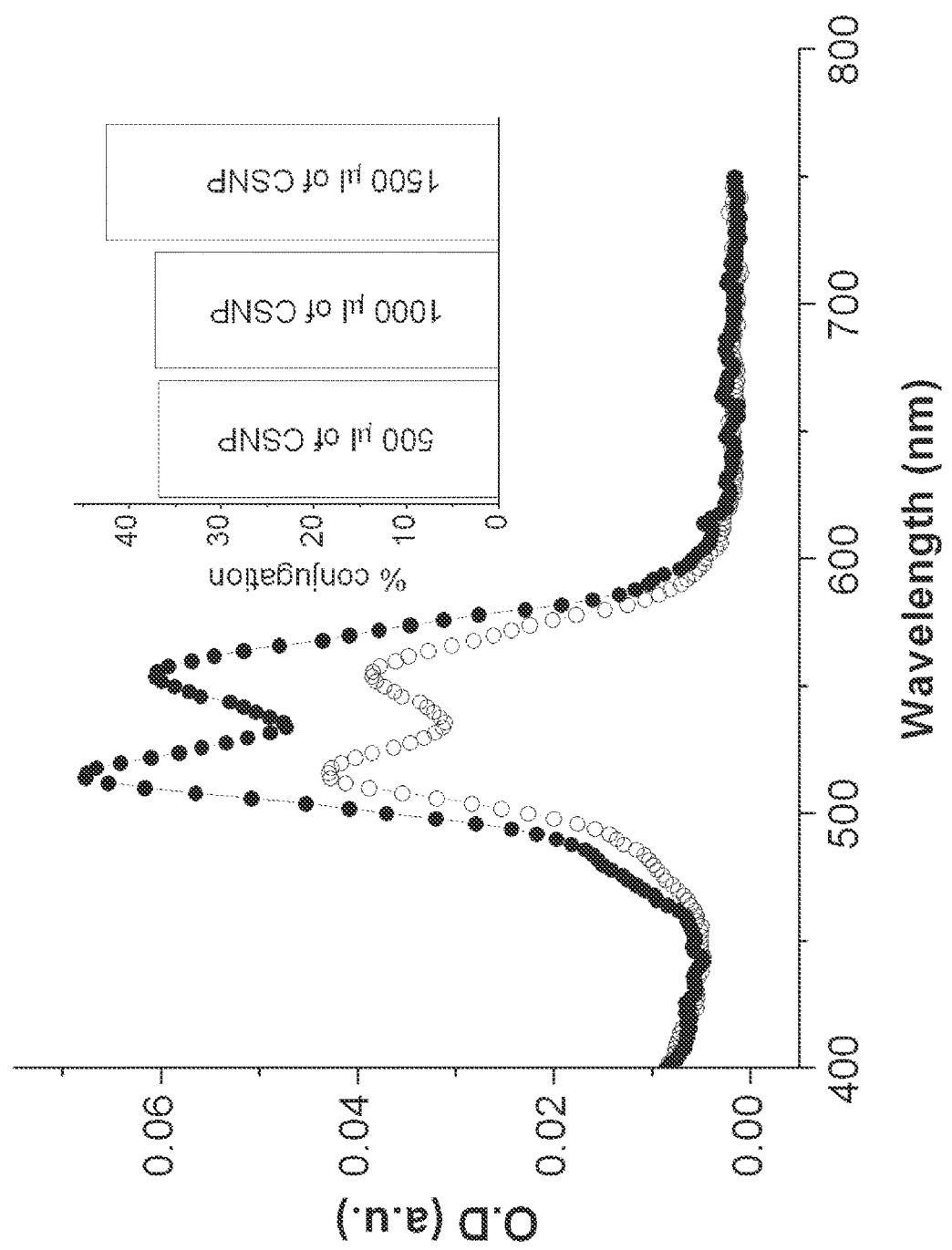
FIG. 14 is an absorbance spectra showing the result of conjugation SA-TMR to gold-coated phosphor CSNP as described in Example 3.

The inset of FIG. 14 shows percent conjugation of SA-TMR. This was calculated by taking the absorbance of the control solutions at 520 nm to be 100. The percentage difference in the absorbance at 520 nm between the supernatant and the control was estimated as the percent of conjugation. As the amount of gold-coated phosphor CSNP was increased in the solution, more SA-TMR was conjugated to gold-coated phosphor CSNP.

Figure 15:
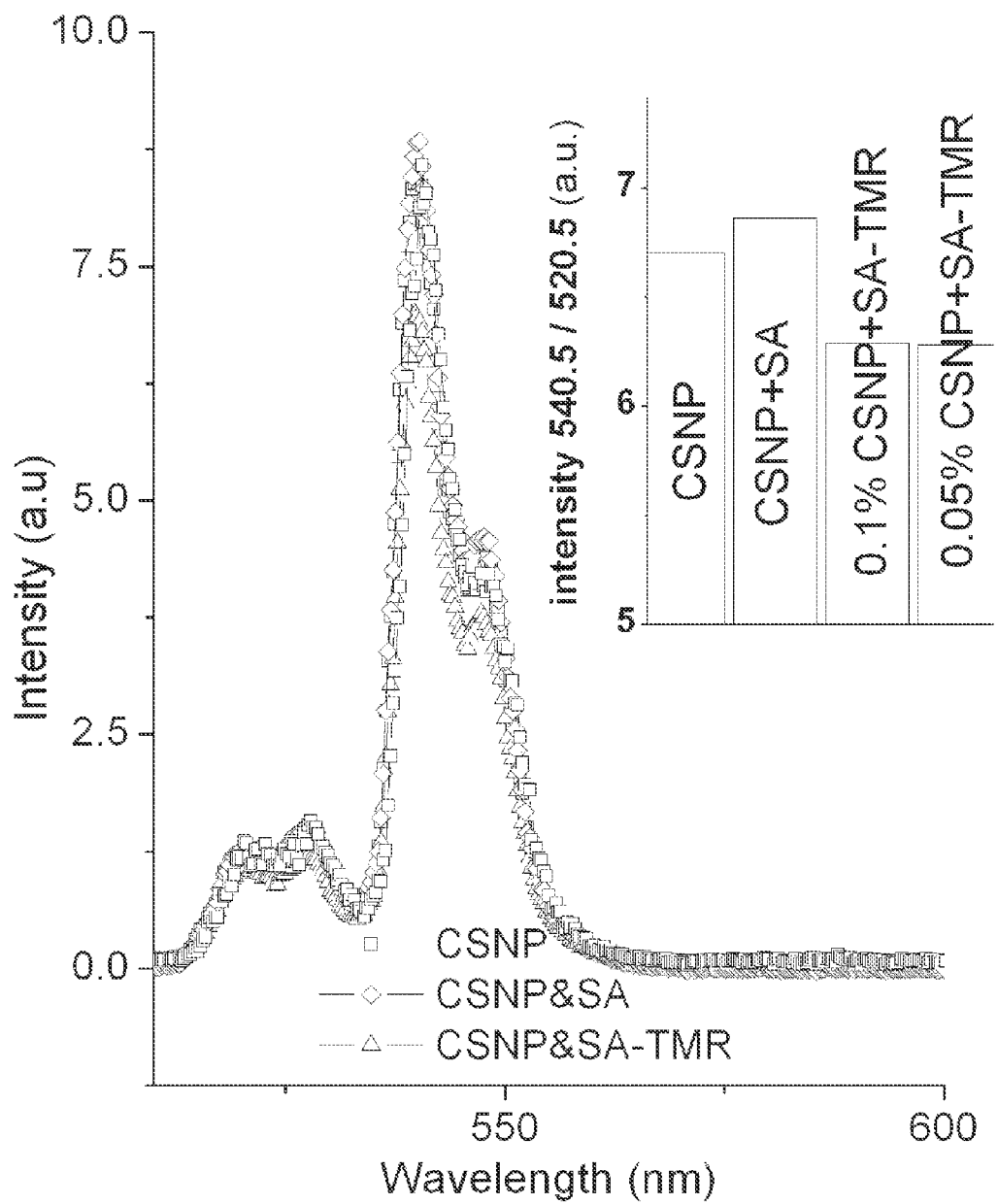
FIG. 15 is an emission spectrum comparing gold-coated phosphor CSNP alone, gold-coated phosphor CSNP conjugated to streptavidin (SA) and gold-coated phosphor CSNP conjugated to SA-TMR as described in Example 3.

These SA-TMR conjugated gold-coated phosphor CSNP were further tested for FRET by depositing the nanoparticles on a microscopic glass slide. Sample handling was designed to minimize photobleaching of the dye. To eliminate any effect from SA, SA was conjugated to gold-coated phosphor CSNP and the phosphorescence compared with nascent gold-coated phosphor CSNP and SA-TMR conjugated to gold-coated phosphor CSNP upon excitation with a 975 nm laser. The resulting spectrum is shown in FIG. 15, wherein the squares represent emission from gold-coated phosphor CSNP, the diamonds represent emission from gold-coated phosphor CSNP conjugated to SA, and the triangles represent emission from the gold-coated phosphor CSNP conjugated to SA-TMR. It was observed that when the gold-coated phosphor CSNP was conjugated to SA alone, the green emission (520.5 and 540.5 nm) did not decrease. This was established by taking the ratio of intensities of emissions at 540.5 and 520.5 nm (ratios of intensities for the samples is shown in the inset of FIG. 15. On the other hand, when SA-TMR conjugated to gold-coated phosphor CSNP was excited with 975 nm laser, the ratio was different. Considering the fact that the laser power was very low and the fact that both nascent and SA-only conjugated gold-coated phosphor CSNP have the same ratios, it is most likely that the change in the ratio is caused by the acceptance of the radiant energy of gold-coated phosphor CSNP by TMR dye. The TMR fluorescence from the resonance energy transfer around 560 nm was not observed.

FRET experiments were performed with a PICOQUANT™ pulsed diode laser operating at 975 nm and 80 MHz available from PicoQuant GmbH, Berlin, Germany. The photons emitted by the upconverting phosphor were focused on to Acton SpectraPro 300i series spectrometer by objective and condensing lenses, and imaged by Princeton Instruments PI-MAX camera fitted with a charge couple device sensor. Both the spectrometer and camera are available from Princeton Instruments, Trenton, N.J.

Figure 16:
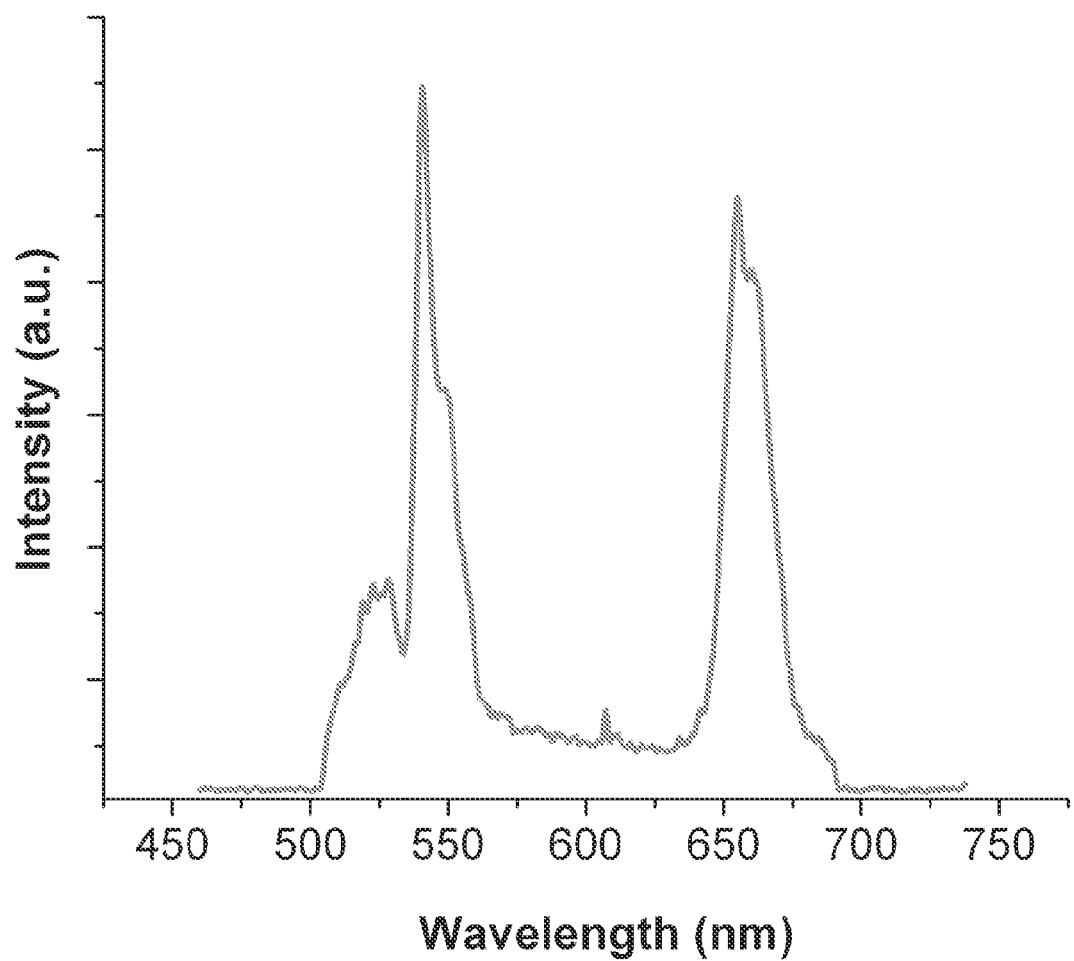
FIG. 16 is an emission spectrum of ALEXA FLUOR™ tagged gold-coated phosphor CSNP excited with 980 nm light.

In another embodiment, the fluorophore conjugated to SA is an ALEXA FLUOR™ available from Invitrogen. The spectrum from gold-coated phosphor CSNP conjugated to streptavidin with the ALEXA FLUOR™ upon excitation at 660 nm is provided in FIG. 16.

Example 4—Gold-Coated CSNPs with Magnetic Component

Magnetic gold-coated phosphor CSNPs are also synthesized by the sol-gel citrate technique described previously. The citrate route for magnetic particles avoids cumbersome synthetic protocols and worrisome incompatible reagents in the solution. This is beneficial when using the resulting nanoparticles in a biomarker platform.

Magnetite gold-coated phosphor CSNPs were prepared by co-precipitation of $Fe_3O_4$ upon addition of $NH_4OH$ solution to a mixture of $FeCl_2$ and $FeCl_3$, taken in a 1:2 molar ratio. The reaction consisted of two steps—1) the precipitation step and 2) the capping step with citric acid. The reaction was performed under Argon flow at 80° C. with vigorous stirring of the solution. The precipitation reaction was initiated by introducing 40 mmoles of $NH_4OH$ into 40 ml water containing 4.3 mmoles of $FeCl_2$ and 8.6 mmoles of $FeCl_3$. The heating was continued for 30 min upon the addition of the $NH_4OH$. 5.2 mmoles of citric acid was then added and the heating continued at an increased temperature of 95° C. for 90 min. Thereafter, the resulting solution was diluted to 1000 ml to give a preferred concentration of 1% $Fe_3O_4$.

The magnetic particles in up-converting phosphors were derived from such stock solutions mentioned above. The precursors used for up-converting phosphors were water soluble salts of a lanthanide. The ratio of concentrations of the lanthanide, $Fe_3O_4$, sodium citrate and sodium fluoride were optimized to incorporate the magnetic particles into the lanthanide matrix. In a typical reaction, 80 mmoles of $Fe_3O_4$ were reacted with 1.56 mmoles of $Y(NO_3)_3$, 0.66 mmoles of $Yb(NO_3)_3$ and 40 micromoles of $Er(NO_3)_3$, amounting to 0.6 M of lanthanum nitrates. Equal volume of 0.6 M sodium citrate and 12 ml of 1M solution of NaF was introduced to form the $NaYF_4$:Yb:Er matrix. The reaction mixture was heated at 90° C. for two hours.

To introduce the gold shell on top of the magnetic core phosphor, a dilute solution of HAuCl4 was introduced to coat the dielectric surface with gold. This procedure is the same as described previously in reference to Examples 1 and 2.

Figure 17:
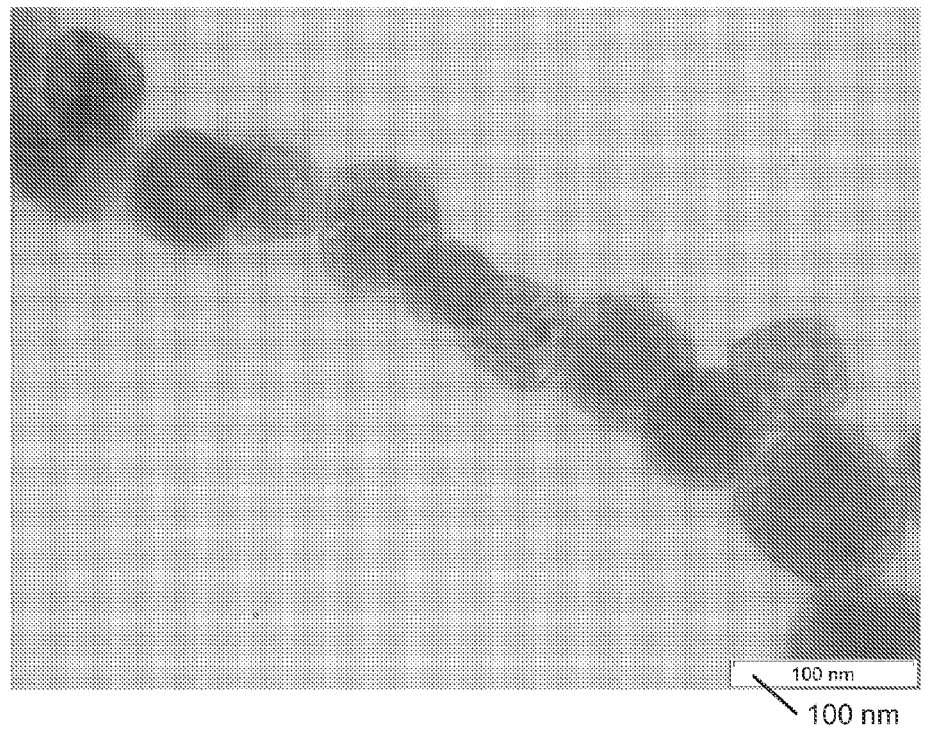
FIG. 17 are bright-field transmission electron micrographs of magnetite containing gold-coated phosphor CSNPs.
Figure 17:
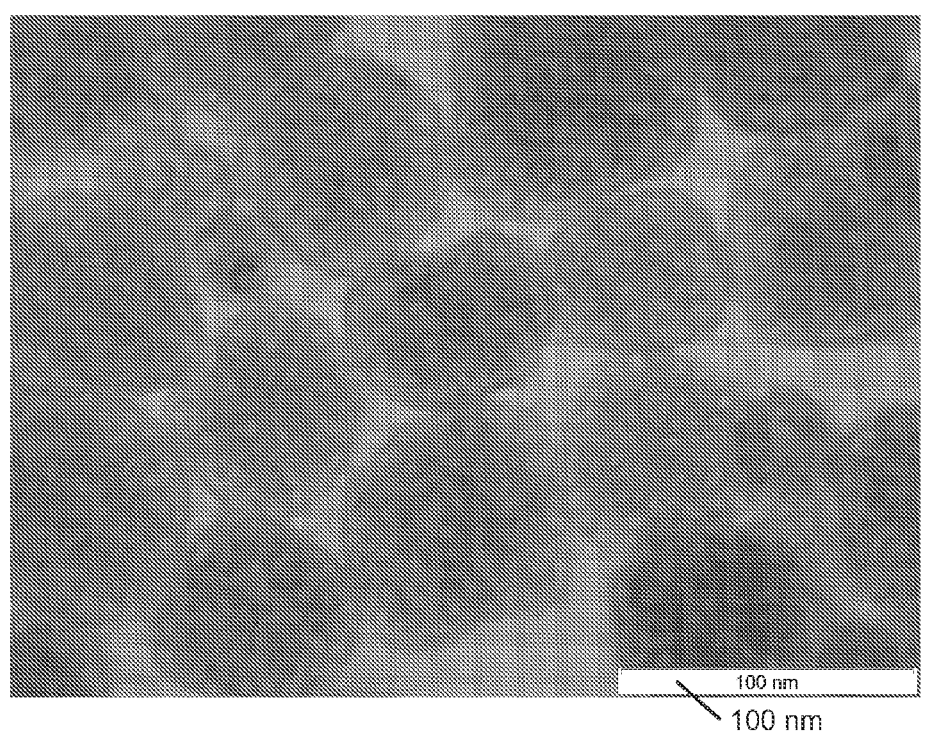

FIGS. 17a and 17b are transmission electron micrographs showing 100 nm nanophosphor, $NaYF_4$:20% Yb:2% Er, with $Fe_3O_4$ core and gold shell. The gold shell is visible as a 5 nm contour around the nanophosphor. The super paramagnetic $Fe_3O_4$ nanoparticles are typically in the 10-15 nm range.

Figure 18:
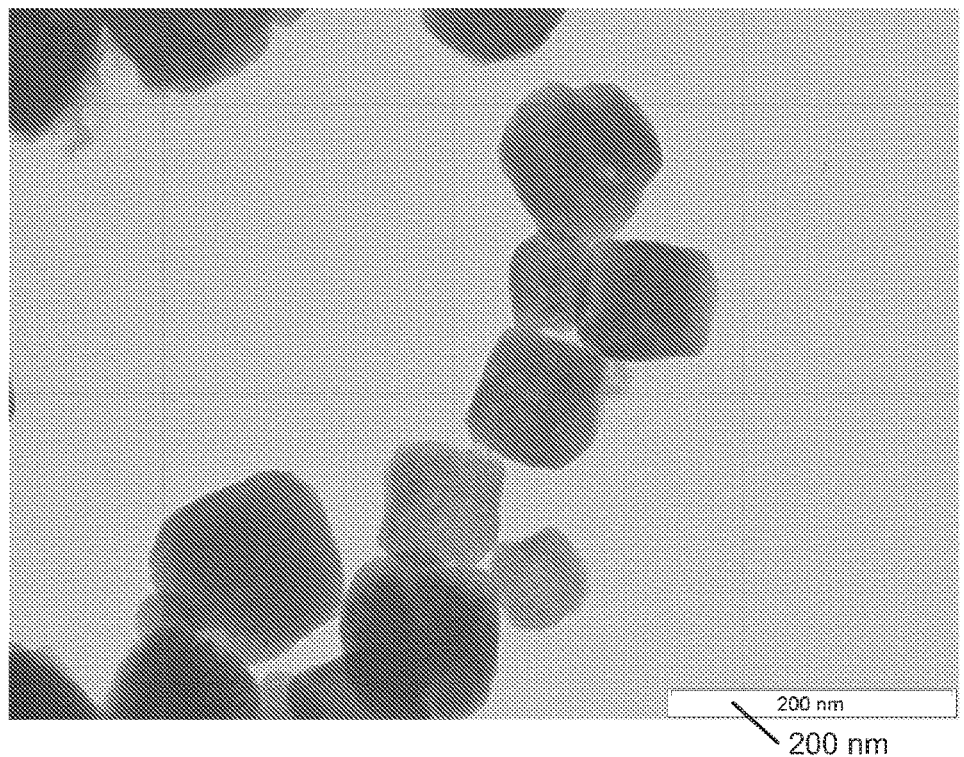
FIG. 18 are bright-field transmission electron micrographs of magnetite containing uncoated phosphor CSNPs.
Figure 18:
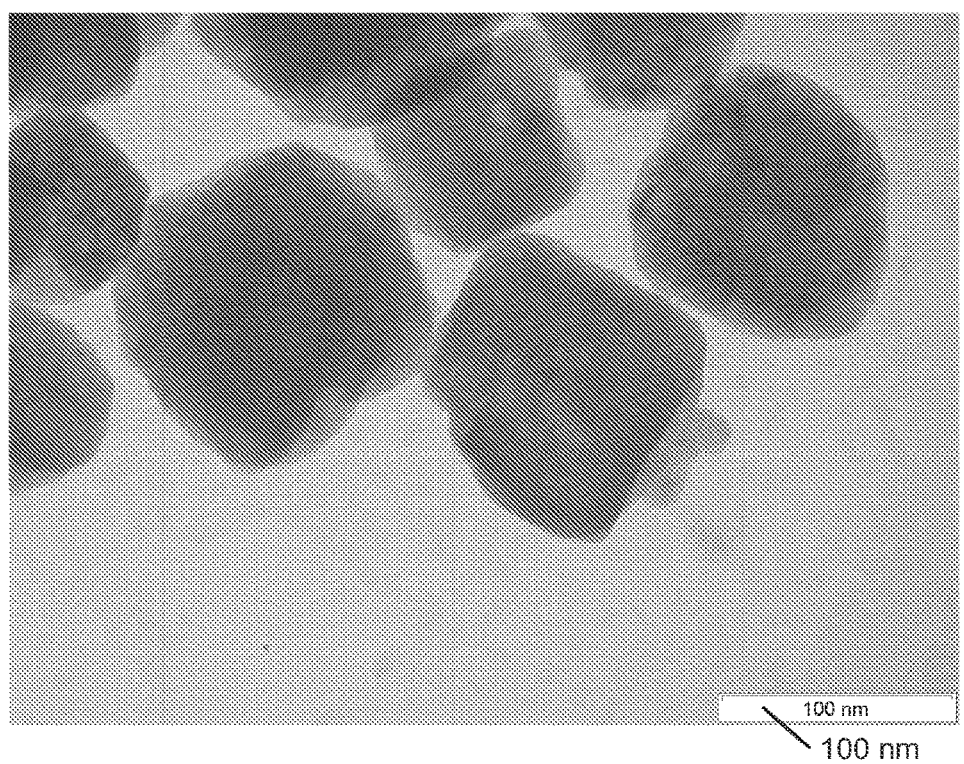

FIGS. 18a and 18b are transmission electron micrographs showing the 100 nm nanophosphor, $NaYF_4$:20% Yb:2% Er, with $Fe_3O_4$ core and without the gold shell.

Figure 19:
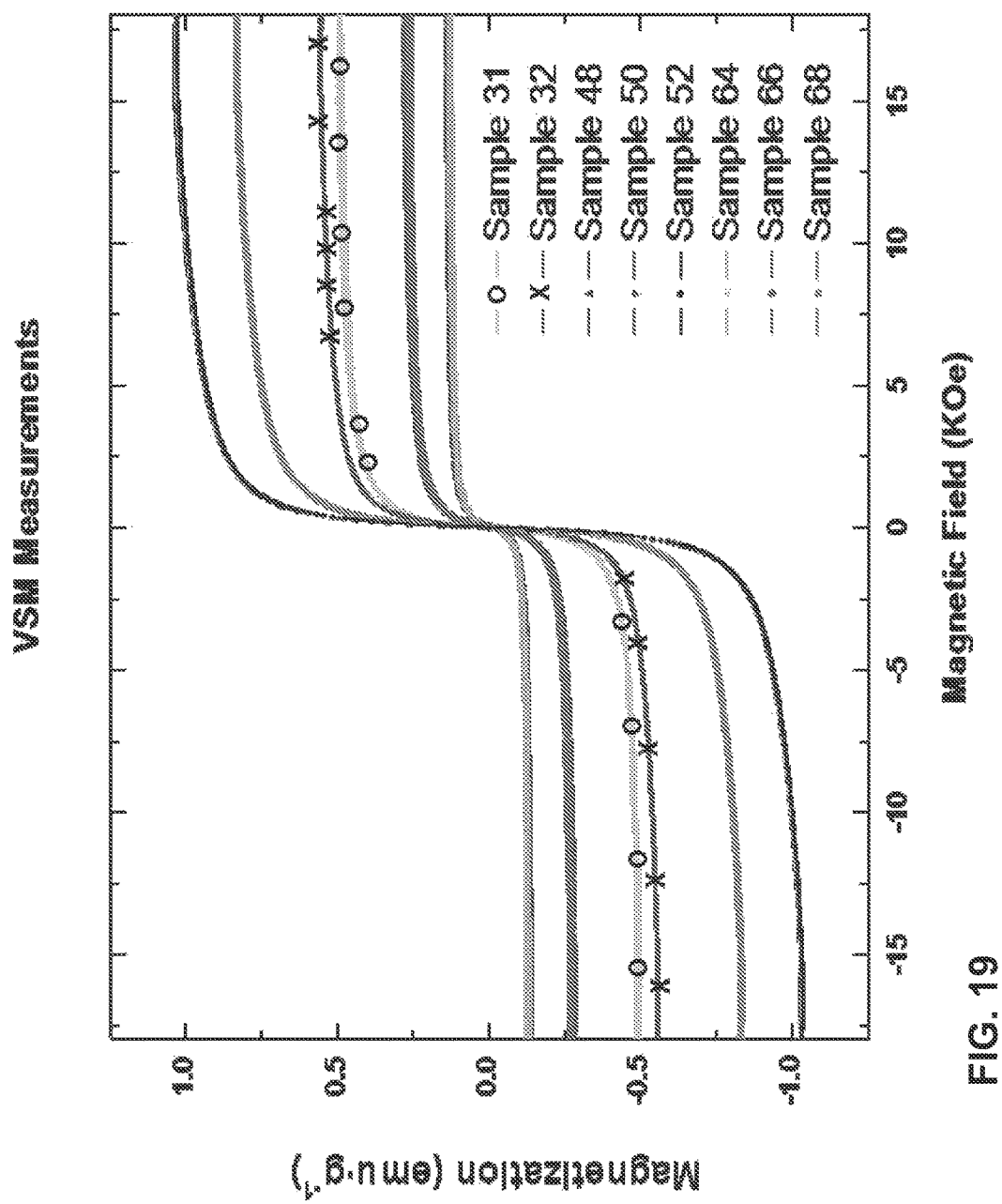
FIG. 19 is a graph of superparamagnetic hysteresis measurements of gold-coated and uncoated phosphor CSNPs with magnetite cores.

FIG. 19 illustrates superparamagnetic hysteresis measurements of 100 nm nanophosphor, $NaYF_4$:20% Yb:2% Er, with $Fe_3O_4$ core and with/without gold shell from a Vibrating Sample Magnetometer. The magnetization curves are shown for various fractions of $Fe_3O_4$ in a 100 nm nanophosphor with 5 nm gold shell. For comparison, uncoated samples were also tested. Sample 32 corresponds to the TEM images shown in FIG. 17, and sample 31 to the uncoated samples represented in FIG. 18.

Example 5—Two-Metal Coated Phosphor CSNP

A bi-metallic shell consisting of Au and Ag was prepared by employing AgNO3 in water.

In a typical reaction, the concentration of the AgNO3 solution was fixed at 0.05 M. The synthesis involved the addition of the AgNO3 solution to the initially reduced gold on the surface of the phosphor.

Figure 20:
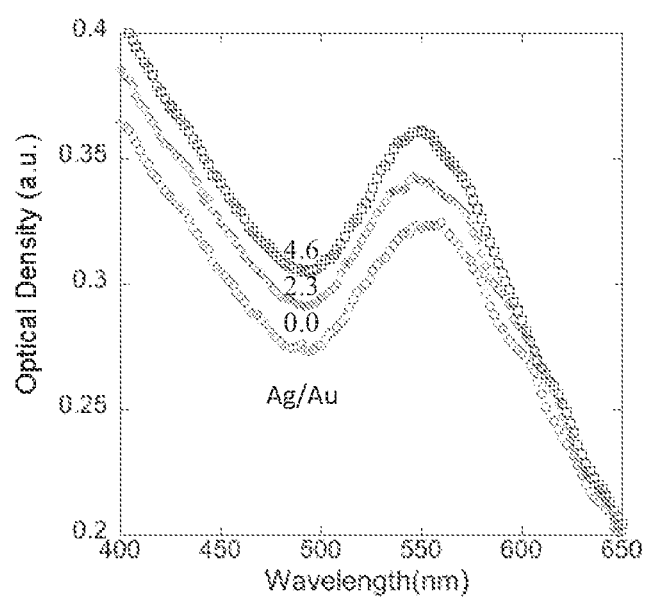
FIG. 20 shows absorbance spectra of three different solutions of $NaYF_4$:20% Yb:2% Er containing different molar ratios of Ag and Au.

In a typically reaction carried out at 90° C., 1 ml, 0.2M of rare earth chlorides were stirred with 2 ml, 0.2M of sodium citrate followed by the addition of 4 ml, 1M sodium fluoride. Addition of the initial gold precursor, 150 μl solution containing 380 nmoles $HAuCl_4$ was followed by the addition of 2.5 μmoles of $AgNO_3$. Two more additions of 380 nmoles of $HAuCl_4$ followed the addition of $AgNO_3$ at intervals of one hour. FIG. 20 shows the absorbance spectra of three different solutions of $NaYF_4$:20% Yb:2% Er containing different molar ratios of Ag and Au.

Example 6—Au/An-Coated CSNPs as Biomarkers

The Au/Ag shell coated phosphor CSNPs can be labeled for use as biomarkers. Labeled Au/Ag-coated phosphor CSNPs such as those prepared in Example 5 are useful as in vivo biomarkers. The Au/Ag coating is an inert platform to which various biological molecules can be attached, such as the SA and SA-TMR. The Au/Ag-coated phosphor CSNPs are excited by a low energy laser which does not harm the biological molecule attached and the surrounding tissues are transparent to this wavelength and therefore the excitation laser does not harm surrounding tissues. Additionally, the low energy of the excitation source minimizes excitation of surrounding molecules, such as proteins, thereby minimizing background fluorescence signals from those surrounding molecules. The nanoparticles do not photo bleach leading to improved sensitivity and reliability of data. The addition of Ag aids in the incorporation of many different fluorophores on the surface, which can be selectively enhanced by the presence of the metal.

Example 7—Temperature Measurement with Au/An-Coated CSNPs

The plasmon resonance of the metal nanoparticle converts the light energy to heat energy (Alexander O. Govorov and Hugh H. Richardson, Nanotoday, 2, 30, 2007). This is observed as an increase in temperature of the matrix inside and the surroundings. The increase in the temperature of the inside matrix when the plasmonic metal is coated as a shell has a square dependence on the radius of the particle. The larger the particle greater is the temperature raise. Also, the stronger the plasmon resonance the greater the increase in the temperature (Lee, J., et al., Nano Lett. 4, 2323, 2004). It is possible to increase and harvest the increase in the temperature by coating gold with silver, which generates 10 times more heat energy than just gold. This allows the use of low power to achieve a certain temperature. Also, coating of silver will increase the possibility to achieve phase transformation in the core and in the surroundings. For example, in the case of phosphor CSNP, the material $NaYF_4$ exists as a meta-stable cubic phase at low temperature. This phase has low up-conversion efficiency. Conversion of the metastable cubic phase to the hexagonal phase is achieved by heating the particles. With silver as one of the metal shell element, bright emissions are selectively achieved through local heating of the phosphor by subjecting the phosphor CSNP to plasmonic excitation. This will open new possibilities with optical actuation and sensing.

The Au/Ag as well as the gold-coated phosphor CSNPs disclosed herein can be used as temperature sensors. Due to the size and the inert nature of the metal shell, the nanoparticles can be used to determine temperature in vivo. The CSNPs are placed in the desired location for determining a temperature and excited with a near infrared laser and the resulting emission is measured. For gold-coated phosphor CSNPs containing $Er^{3+}$ and $Tm^{3+}$, the two emission peaks of interest occur at 520 and 540 nm. From the ratio of the intensities of the emission at those two wavelengths temperature is determined. Using spectroscopic term symbols, the electronic excitation from the ground state 4I15/2 to the 4F7/2 state populates two lower states $^2H_{11/2}$ and $^4S_{3/2}$ based on the Boltzmann distribution, which is influenced by the temperature of the particle. The emission intensities at 520 and 540 nm are then incorporated into the following equation: $\log [\text{Intensity}(520)/\text{Intensity}(540)]=A+(B/T)$, where A and B are constants for $Er^{3+}$ and $Tm^{3+}$, and T is the absolute temperature measured in degree Kelvin. Due to the increased heat generation with silver, a Au/Ag-coated CSNP is more useful for temperature measurement than a gold-coated phosphor CSNP.

Gold-coated and Au/Ag-coated nanoparticle temperature sensors are useful in monitoring temperature in microfluidic devices and studying individual cell thermogenics. Additionally, they could be used to determine the denaturation temperature of single protein molecules and individual double strand DNA hybridization temperatures.

Hyperthermic cancer therapy is another area where temperature monitoring in small spaces is relevant. There is currently a lack of precise knowledge about the amount of heat delivered to the cancerous cells and having such knowledge is important to the efficacy of the therapy. Gold-coated or Au/Ag-coated phosphor CSNPs could be introduced to the site of the tumor prior to the start of the hyperthermic therapy. As heat is being applied, the gold-coated or Au/Ag-coated phosphor CSNPs are excited and their emission measured to keep the physician informed of the amount of heat actually present at the site of the therapy.

Example 8—Hyperthermic Cancer Therapy with Au/An-Coated CSNPs

In addition to temperature measurement in hyperthermic therapy, Au/Ag-coated phosphor CSNPs can act as heat actuator and thus deliver heat to the area where therapy is needed. There is a lack of safe and accurate delivery and actuation of heat in vivo. Because Au/Ag-coated phosphor CSNPs operate as temperature sensors, they can both deliver the heat and allow for monitoring of the resulting temperature.

Example 9—Au/An-Coated CSNPs as Anti-Counterfeiting Measure in Security Papers Security paper is any paper that incorporates one or more features that can be used to identify the paper and therefore identify any item that incorporates the security paper as an original. Examples of items that incorporate security paper include, but are not limited to, currency, stock certificates, birth certificates, checks, academic certificates, passports, titles to property, lottery tickets, and legal documents.

Gold-coated phosphor CSNPs are an excellent feature to include in security paper. The gold-coated phosphor CSNPs have a reddish color that is visible to the naked eye. Upon excitation with near-infrared laser, light is emitted. The emitted light can be in the red, blue or green wavelengths. If light of multiple wavelengths is emitted, the emitted light may appear to be a combination of red, blue or green to the observer. For example, if the emitted light is in the red and blue wavelengths, it would appear purple to the observer. Near-infrared lasers can be handheld devices and are safe to operate. Therefore, gold-coated phosphor CSNPs are an excellent solution for authenticating items incorporating paper.

Adding silver to the shell to make a Au/Ag-coated phosphor CSNP adds functionality as more colors can be used.

The nanoparticles can be incorporated into the paper during its manufacture or after manufacture by printing them onto the paper. Ink jet printing is an excellent option for printing the nanoparticles in an ink. The Au/Ag shell can have various modifications attached that would be allow for tuning the properties of the ink to optimize the printing—surface tension, viscosity, etc. Current ink jet printing technology allows for printing on nanoscale as reported by Duncan Graham-Rowe in MIT's Technology Review on Sep. 13, 2007. The printed nanoparticles can therefore be so small as to require magnification to detect. Additionally, the nanoparticles can be printed in a pattern or text and because of the nanoscale resolution, a very large amount of information can be placed on the paper in a small space. Because each rare earth element has a unique excitation wavelength, the authentication technique can be tailored by using different rare earth elements in the upconverting phosphor core.

REFERENCES

1. J. C. Boyer, L. A. Cuccia, and J. A. Capobianco, "Synthesis of colloidal upconverting $NaYF4:Er^{3+}/Yb^{3+}$ and $Tm^{3+}/Yb^{3+}$ monodisperse nanocrystals," Nano Letters, 7(3), 847-852 (2007).
2. H. X. Mai, Y. W. Zhang, R. Si et al., "High-quality sodium rare-earth fluoride nanocrystals: Controlled synthesis and optical properties," Journal of the American Chemical Society, 128(19), 6426-6436 (2006).
3. G. S. Yi, H. C. Lu, S. Y. Zhao et al., "Synthesis, characterization, and biological application of size-controlled nanocrystalline NaYF4:Yb,Er infrared-to-visible up-conversion phosphors," Nano Letters, 4(11), 2191-2196 (2004).
4. K. Kuningas, T. Rantanen, T. Ukonaho et al., "Homogeneous assay technology based on upconverting phosphors," Analytical Chemistry, 77(22), 7348-7355 (2005).
5. F. Vetrone, and J. A. Capobianco, "Lanthanide-doped fluoride nanoparticles: luminescence, upconversion, and biological applications," International Journal of Nanotechnology, 5(9-12), 1306-1339 (2008).
6. L. Y. Wang, R. X. Yan, Z. Y. Hao et al., "Fluorescence resonant energy transfer biosensor based on upconversion-luminescent nanoparticles," Angewandte Chemie-International Edition, 44(37), 6054-6057 (2005).
7. K. Aslan, J. R. Lakowicz, and C. D. Geddes, "Metal-enhanced fluorescence using anisotropic silver nanostructures: critical progress to date," Analytical and Bioanalytical Chemistry, 382(4), 926-933 (2005).
8. Y. Fu, J. Zhang, and J. R. Lakowicz, "Plasmonic enhancement of single-molecule fluorescence near a silver nanoparticle," Journal of Fluorescence, 17(6), 811-816 (2007).
9. Z. Y. Ma, D. Dosev, and I. M. Kennedy, "A microemulsion preparation of nanoparticles of europium in silica with luminescence enhancement using silver," Nanotechnology, 20(8), (2009).
10. G. Schneider, G. Decher, N. Nerambourg et al., "Distance-dependent fluorescence quenching on gold nanoparticles ensheathed with layer-by-layer assembled polyelectrolytes," Nano Letters, 6(3), 530-536 (2006).
11. J. Zhang, R. Badugu, and J. R. Lakowicz, "Fluorescence Quenching of CdTe Nanocrystals by Bound Gold Nanoparticles in Aqueous Solution," Plasmonics, 3(1), 3-11 (2008).
12. M. Lessard-Viger, M. Rioux, L. Rainville et al., "FRET enhancement in multilayer core-shell nanoparticles," Nano Lett, 9(8), 3066-71 (2009).
13. S. J. Pennycook, M. Varela, C. J. D. Heterington, A. I. Kirkland, *Materials Research Science Bulletin* 2006, 31, 36-43.
14. K. R. Brown, D. G. Walter, M. J. Natan, *Chemistry of Materials* 2000, 12, (2), 306-313.
15. Zhang, H., Li, Y., Ivanov, I., Qu, Y., Huang, Y. and Duan, X., Angew. Chemie, 2010, 49, 2865-2868.
16. S. Schietinger, T. Aichele, H. Q. Wang, T. Nann, O. Benson, *Nano Letters* 2010, 10, (1), 134-138.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

We claim:
1. A nanoparticle comprising:
    a phosphorescent core comprising: $Er^{3+}$, $Y^{3+}$, $Yb^{3+}$, sodium cation, citrate anion, and fluoride anion; and
    a streptavidin (SA) or streptavidin-tetramethylrhodamine (SA-TMR) tag; and
    a metal shell comprising Au and Ag; and
    a magnetic component comprising $Fe_3O_4$.
2. The nanoparticle of claim 1, wherein the phosphorescent core comprises 20% Yb and 2% Er and $NaYF_4$.
3. The nanoparticle of claim 1, wherein the molar ratio of Ag to Au is 4.6 to 1.
4. A method of producing a nanoparticle comprising a phosphorescent core and a two-metal shell, the method comprising:
    mixing $Er^{3+}$, $Y^{3+}$, and $Yb^{3+}$ with sodium citrate to create a citrate solution;
    mixing the citrate solution with sodium fluoride to create a first mixture;
    heating the first mixture;
    adding Au to the first mixture to create a second mixture;
    adding Ag to the second mixture;
    optionally adding Au and adding Ag one or two more times, thereby producing the nanoparticle.
5. The method of claim 4, wherein the Ag is $AgNO_3$.
6. The method of claim 5, wherein the Au is $HAuCl_4$.
7. A nanoparticle made by the method of claim 4.
8. The nanoparticle of claim 1, wherein the phosphorescent core comprises 20% Yb and 2% Er and $NaYF_4$, and the molar ratio of Ag to Au is 4.6 to 1.
9. The method of claim 4, wherein the Ag is $AgNO_3$ and the Au is $HAuCl_4$.
10. A nanoparticle made by the method of claim 5.
11. A nanoparticle made by the method of claim 6.
12. A nanoparticle made by the method of claim 9.

* * * * *